(12) United States Patent
Ye et al.

(10) Patent No.: US 6,733,992 B2
(45) Date of Patent: May 11, 2004

(54) ISOLATED HUMAN RAS-LIKE PROTEINS, NUCLEIC ACID MOLECULES ENCODING THESE HUMAN RAS-LIKE PROTEINS, AND USES THEREOF

(75) Inventors: Jane Ye, Boyds, MD (US); Karen A. Ketchum, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 232 days.

(21) Appl. No.: 09/788,654

(22) Filed: Feb. 21, 2001

(65) Prior Publication Data

US 2002/0119920 A1 Aug. 29, 2002

(51) Int. Cl.[7] ............................................. C12N 15/00
(52) U.S. Cl. .................... 435/69.1; 536/23.1; 536/23.5; 435/320.1; 435/325
(58) Field of Search ............................ 536/23.5, 23.1, 536/24.1; 435/320.1, 325, 69.1

(56) References Cited

FOREIGN PATENT DOCUMENTS

| WO | WO 02 29039 A | 4/2002 |
|----|---------------|--------|
| WO | WO-200229039 A2 * | 4/2002 |

OTHER PUBLICATIONS

Database Sptrembl 21, Accession No. Q96S79, Hayashi A, et al., Dec. 1, 2001 (see USPTO search report US–09–788–654a–2.rspt, result 1).*

United States patent application No. 20020150916–A1, Meyers R, Oct. 17, 2002.*

Boehringer Mannheim Biochemical 1994 Catalog, p. 93.*

Saito et al. Database EMBL Online! "*Homo Sapiens* mRNA for Ras–Like Protein/VTS58635, Complete CDs." Database accession No. AB047296. XP002228169.

Shimkets RA et al. "Human ORFX2604 Polypeptide Sequence SEQ ID NO: 5208." Feb. 8, 2001. Database accession No. AAB42840. XP002228170.

Shimkets RA et al. "Human ORFX ORF2604 Polynucleotide Sequence SEQ ID NO: 5207." Feb. 8, 2001. Database accession No. AAC77049. XP002228171.

Database EMBL Online! "*Homo Sapiens* cDNA Clone." National Institutes of Health. Dec. 14, 2000. Database accession No. BF526898. XP002228172.

Database EMBL Online! "*Homo Sapiens* cDNA Clone." National Cancer Institute. Jul. 30, 2000. Database accession No. BE467359. XP002228173.

* cited by examiner

*Primary Examiner*—Anthony C. Caputa
*Assistant Examiner*—Stephen L. Rawlings
(74) *Attorney, Agent, or Firm*—Celera Genomics; Justin D. Karjala

(57) ABSTRACT

The present invention provides amino acid sequences of polypeptides that are encoded by genes within the human genome, the Ras-like protein polypeptides of the present invention. The present invention specifically provides isolated polypeptide and nucleic acid molecules, methods of identifying orthologs and paralogs of the Ras-like protein polypeptides, and methods of identifying modulators of the Ras-like protein polypeptides.

9 Claims, 11 Drawing Sheets

```
   1 CCTCGGCGGC CCGCATCTGC CCCCGCGCGC CCGCCCTGAG CCCGCCCCGA
  51 CTGGGCAGGC GGGGGAGCCC CTACTTCTCT CCCCCCGGGC GGGGGAGCCG
 101 GGGGCAGCG CCGGAGCCCG GGGGAGCTC AGCCCCGCCG ACCGGCCGGC
 151 CAGGGCAGGG GGCAGCTAGG ACGGCCCCGG TCCAGGTGGA GGCCGCAGAG
 201 GGCCCAGGGC AAGCAGAGGC AGCAATGGTT GGTCCTGACG GTGGCTGAGC
 251 CCCCAGCCCC TGGAATATGC AGCCCGGGGG AGCCCCAGAC AGCGGCAAGG
 301 ACGAGGTGGC GGAGTGGGGC GGGAGGCATG GTCTCCACCT ACCGGGTGGC
 351 CGTGCTGGGG GCGCGAGGTG TGGGCAAGAG TGCCATCGTG CGCCAGTTCT
 401 TGTACAACGA GTTCAGCGAG GTCTGCGTCC CCACCACCGC CCGCCGCCTT
 451 TACCTGCCTG CTGTCGTCAT GAACGGCCAC GTGCACGACC TCCAGATCCT
 501 CGACTTTCCA CCCATCAGCG CCTTCCCTGT CAATACGCTC CAGGAGTGGG
 551 CAGACACCTG CTGCAGGGGA CTCCGGAGTG TCCACGCCTA CATCCTGGTC
 601 TACGACATCT GCTGCTTTGA CAGCTTTGAG TACGTCAAGA CCATCCGCCA
 651 GCAGATCCTG GAGACGAGGG TGATCGGAAC CTCAGAGACG CCCATCATCA
 701 TCGTGGGCAA CAAGCGGGAC CTGCAGCGCG GACGCGTGAT CCCGCGCTGG
 751 AACGTGTCGC ACCTGGTACG CAAGACCTGG AAGTGCGGCT ACGTGGAATG
 801 CTCGGCCAAG TACAACTGGC ACATCCTGCT GCTCTTCAGC GAGCTGCTCA
 851 AGAGCGTCGG CTGCGCCCGT TGCAAGCACG TGCACGCTGC CCTGCGCTTC
 901 CAGGGCGCGC TGCGCCGCAA CCGCTGCGCC ATCATGTGAC GCCTGCGCGC
 951 CCCTCGGGCT GCACCGGCAC TGGCCGAGCG GAGGGCGGGG CCGTACTGCG
1001 GGGCTGGGGC GGGGAGCGGG CGGGAAATGG AACTGTGACG GTCCCGGCCT
1051 GAGGCCCCTG CAGCCACGCA CCTCCCGGTG AGAAGCAGAG CGCGAGAGGG
1101 AGCCCTCCGT AACTGCCCAG CCCTGCCCCT TGCCCCGTG GCTTCCTGGG
1151 ACAGCCGCCT TCAGTGCTGT ATTTAGTGCA GTGCCCGGCC CGACCCGCGG
1201 GGGTGCCACA GCCTTTTGGG ATGGGGGTGA GCGTGCAATG GAGGCTGGGG
1251 GTGGCGAGGT GCCGCCTTGG CCGGGCCCCC ACGTGTCTTC TCCAGAATGT
1301 GTCTGTCTTT GCCTGGTGTC TTCCTTTCCC GTGTCCGCCC ACCCCAGCGT
1351 CTGTTGGTAC TTACCTGTCT CACCTACCCT CCAGTCCCCT CCCAGCTCCG
1401 CTCACAGGGC TCTCATTTCG TCCATCCCCT TGTCGCAGAT CCTGGCAGCT
1451 TCTTTGTGAG GCCAGGCCTT CTGACTGTCA GCACCACCGG CACAGGGCAG
1501 AGATGCGGGT GGCCCAAGGA CCACGATCAA GGGGTCCGGG GGACCGAGGT
1551 CCCAGATCAG TGAGGGGAGA AGGTTGAGCT CTCCGGCTTC CAGGGAGACC
1601 TCCCCGCCCA GCAGCCCCCA GAGACACAAC AACCTACCTT CCAGCCTTAA
1651 CTCGATGGTC CGTCCCTGCC AGGTGCCCCT CACTCTTCCT GACCCCAAAG
1701 CCAGATCACC CCCTGGGTTA AAACTTTTTT TCTTTTTTTT TTTTGGACAG
1751 AGTGTGGAAA GGGAGCCCCC CAAAGGATAG CTTCTTTTTC ATGATGCCAG
1801 GCTCCAGTCC TTTATTCCCT TCTGCATACT GCAATCTGAT CTGTCAGACT
1851 GGGGAATGTT GGGTTCTGGG GTCTGGTCGT GGGCAGGATG GTGCCCAGAA
1901 GGGGGTTAGG TTGTCCCAGT GAAATTCTG TTGCCCCGTC TCAACCCCAT
1951 CTGACTACCC CAGACTCTGC CTGCCTCAGA TCTCAGACTA TCCTGATTAA
2001 TCTGGGAAG AACAGAGCCA GGGAAAGAAT GGTGGGACC CCTGTACTTG
2051 GGGGAGACAC ACCTGCATCT TCCTCCTGCC ACAGATGGAG GCCCTCAGGA
2101 TCTGACACCC TCTTGTCCCA ACACCAGTCA GCCCTATACC CTAACTCACT
2151 CCACCCCATT TTCTCCGGCT GCCTGGCCGG GTTTCTACCT CTCGTCACCG
2201 GAGCTGATCA CTGTCAGTTT TGTACCGATT TAGAAATAAC AATAATAATG
2251 AAGATTCTAG GAATGGCATG AGGGATTGAT GGGGACTTG GAGGGAGGGA
2301 CAAGTGGTGC CCTGTCCCCT GCTCCCCTGG CCAAAGAAAG CTGTCCTTGA
2351 GGCTGAGCCC TCAGCCCTGG CCTGGTGGGG GACAGCAAG GTCCCTTGTT
2401 ATAAGAGGGG CAGAGAGGAC AACTCCGCTT TGGCCAACCT AGCCAAGGCT
2451 GCAGCATATA GACCAGGAAA TCAGGTAGCC CAGACTGGTG ATGGAGCAGA
2501 GTCTGGGGGA AGGGTCGTGG GTGGGGAATT TATCACCAAC ATCCATTGTA
2551 GGGGAATCT ATGATTCTGC TTCCCAGCG GATTCCCACT CTGTCCACCA
2601 AGTGGGGGT AGCACAGCCT CACAGACC GCCCTGACCT TGGGCAGTCT
2651 AGTGTTCCTG CATTCTAGTC CCTGCTGTGC TGCAGGACTT TGGGCAAGTG
2701 ACCTGCCCTC TGTGAGCCTC CCTCTGACAC AGAGGAGGTG GCTCCCCTTC
2751 CCCACACCTT AGAGTGGCTG GGAGGGTAAC AAAGAGGGCC TGCCCCTTTA
2801 GTCTCCTGCA CCCCTGCCCC CTGGTTCACC AGAGGGAGCG GATGAAGGAT
2851 GGCAGCATCT CACATGCCCC ATCACCAACT CTGAGGCACC TGGGGTGGGG
2901 GGGCGGAGCC CAGGCCTCTG GCTGCTCCCC TGTGGGAGCC ATTGGAATGT
2951 ATCCCCTGAC AGGCCCCCTT CCGCCTCCAC CTCAACCCAG GTCTTGGATT
3001 TCAGGTCCCT CCACCCCCAT TCTGAGTCTC TGTCCTTCTC CTTCCACCCG
3051 CTCCCAGGGT TTCCCACCAC AGGGTCTGGA AGTGTGTGTG ACGCCCATTG
```

FIGURE 1A

```
3101 AGCTGTTACC CGAAGTCAGA TTAAAAATCA GGGAGTGTTT TCCCTCGTTT
3151 CTGTAAAAAA AAAAAAAAAA AAAAAAAAAA AAAAAAAAAA AA    (SEQ ID NO:1)
```

FEATURES:
5'UTR:          1-327
Start Codon:    328
Stop Codon:     937
3'UTR:          940

Homologous proteins:
Top 10 BLAST Hits

```
                                                              Score    E
CRA|18000005055410 /altid=gi|5454030  /def=ref|NP_006468.1| RAS-...    199   1e-49
CRA|18000004990267 /altid=gi|7438395  /def=pir||T15833 hypotheti...     89   3e-16
CRA|18000005229906 /altid=gi|4884048  /def=emb|CAB43324.1| (AL05...     86   2e-15
CRA|18000005189812 /altid=gi|9297040  /def=sp|O94363|RHEB_SCHPO ...     85   3e-15
CRA|89000000193051 /altid=gi|7290026  /def=gb|AAF45493.1| (AE003...     84   1e-14
CRA|89000000198900 /altid=gi|7296750  /def=gb|AAF52029.1| (AE003...     83   2e-14
CRA|87000001027207 /altid=gi|7323471  /def=gb|AAF59545.1| (AC024...     82   4e-14
CRA|40000057438157 /altid=gi|10119859 /def=dbj|BAB13483.1| (AB0...      81   7e-14
CRA|18000004932656 /altid=gi|6981476  /def=ref|NP_037348.1| Ras ...     81   9e-14
CRA|18000004905102 /altid=gi|5032041  /def=ref|NP_005605.1| Ras ...     81   9e-14
```

BLAST dbEST hits:
gi|10220573 /dataset=dbest /taxon=96...                                444   e-122

EXPRESSION INFORMATION FOR MODULATORY USE:
library source:
Expression information from BLAST dbEST hits:
gi|10220573 Lung small cell carcinoma Expression information from PCR-based tissue screening panels:
Whole brain

FIGURE 1B

```
  1 MVSTYRVAVL GARGVGKSAI VRQFLYNEFS EVCVPTTARR LYLPAVVMNG
 51 HVHDLQILDF PPISAFPVNT LQEWADTCCR GLRSVHAYIL VYDICCFDSF
101 EYVKTIRQQI LETRVIGTSE TPIIIVGNKR DLQRGRVIPR WNVSHLVRKT
151 WKCGYVECSA KYNWHILLLF SELLKSVGCA RCKHVHAALR FQGALRRNRC
201 AIM  (SEQ ID NO:2)
```

FEATURES:
Functional domains and key regions:
[1] PDOC00001 PS00001 ASN_GLYCOSYLATION
N-glycosylation site 142-145  NVSH  (SEQ ID NO:5)

[2] PDOC00005 PS00005 PKC_PHOSPHO_SITE
Protein kinase C phosphorylation site

Number of matches: 5
    1        4-6    TYR
    2       37-39   TAR
    3     105-107  TIR
    4     150-152  TWK
    5     159-161  SAK

[3] PDOC00006 PS00006 CK2_PHOSPHO_SITE
Casein kinase II phosphorylation site 70-73  TLQE  (SEQ ID NO:6)

[4] PDOC00008 PS00008 MYRISTYL
N-myristoylation site

Number of matches: 2
    1     14-19   GVGKSA  (SEQ ID NO:7)
    2    178-183  GCARCK  (SEQ ID NO:8)

[5] PDOC00266 PS00294 PRENYLATION
Prenyl group binding site (CAAX box)

200-203  CAIM  (SEQ ID NO:9)

[6] PDOC00017 PS00017 ATP_GTP_A
ATP/GTP-binding site motif A (P-loop)

11-18  GARGVGKS  (SEQ ID NO:10)

FIGURE 2A

BLAST Alignment to Top Hit:
```
>CRA|18000005055410 /altid=gi|5454030 /def=ref|NP_006468.1|
          RAS-related on chromsome 22 [Homo sapiens] /org=Homo
          sapiens /taxon=9606 /dataset=nraa /length=203
          Length = 203

Score =  199 bits (501), Expect = 1e-49
 Identities = 105/204 (51%), Positives = 134/204 (65%), Gaps = 1/204 (0%)
 Frame = +1

Query: 328 MVSTYRVAVLGARGVGKSAIVRQFLYNEFSEVCVPTTARRLYLPAVVMNGHVHDLQILDF 507
           M + RVAVLGA GVGK+AI+RQFL+ ++ E   PT   RLY PAV+++G V+DL I D
Sbjct: 1   MGGSLRVAVLGAPGVGKTAIIRQFLFGDYPERHRPTDGPRLYRPAVLLDGAVYDLSIRDG 60

Query: 508 PPIS-AFPVNTLQEWADTCCRGLRSVHAYILVYDICCFDSFEYVKTIRQQILETRVIGTS 684
               +EW D     L+    A++LVYDIC  DSF+YVK +RQ+I ETR   G
Sbjct: 61  DVAGPGSSPGGPEEWPDAKDWSLQDTDAFVLVYDICSPDSFDYVKALRQRIAETRPAGAP 120

Query: 685 ETPIIIVGNKRDLQRGRVIPRWNVSHLVRKTWKCGYVECSAKYNWHILLLFSELLKSVGC 864
           E PI++VGNKRD QR R  PR  ++ LVR+ W+CGY+ECSAKYNWH+L LF ELL+
Sbjct: 121 EAPILVVGNKRDRQRLRFGPRRALAALVRRGWRCGYLECSAKYNWHVLRLFRELLR-CAL 179

Query: 865 ARCKHVHAALRFQGALRRNRCAIM 936    (SEQ ID NO:2)
           R + H ALR QGAL   RC++M
Sbjct: 180 VRARPAHPALRLQGALHPARCSLM 203    (SEQ ID NO:4)
```

Hmmer search results (Pfam):

| Model | Description | Score | E-value | N |
|---|---|---|---|---|
| PF00071 | Ras family | 44.3 | 4.9e-12 | 2 |
| CE00060 | CE00060 rab_ras_like | 11.1 | 0.054 | 1 |
| PF01118 | Semialdehyde dehydrogenase | 4.4 | 1.4 | 1 |

Parsed for domains:

| Model | Domain | seq-f | seq-t | | hmm-f | hmm-t | | score | E-value |
|---|---|---|---|---|---|---|---|---|---|
| PF01118 | 1/1 | 5 | 14 | .. | 1 | 10 | [. | 4.4 | 1.4 |
| PF00071 | 1/2 | 6 | 36 | .. | 1 | 31 | [. | 22.2 | 1.7e-05 |
| CE00060 | 1/1 | 87 | 138 | .. | 99 | 150 | .. | 11.1 | 0.054 |
| PF00071 | 2/2 | 89 | 161 | .. | 76 | 157 | .. | 22.1 | 1.8e-05 |

FIGURE 2B

```
   1 GGCGAACGTG GTTGGAACAA ACAGCTGGCA GACTTGTGAC CCGGCCCTCG
  51 GGATCCGCGA AGCCCCGCT CTCAGCCTTG GGCAGCGACC CAGGTGTCCA
 101 GACGCAGGGA AGGGGACGGA ACCAGGCTTC GCCCCTGTG TGTGTCTCTG
 151 GTCTCTTGCC TCTCTTTCCG GGCAGTCTCT TGCCGGGCGC TGTCTGCAGA
 201 CTCACTGCAG AGCGCAGGCC TTGGGGAGAA AGCGCTCAGG GGCCTGGGCC
 251 CTGCTTCCTG GGACAGCCCC CTCCCTTCCG CACTCAGCCA AGGGTGTTGG
 301 ATTAATATAC TCTTAGATCC AGGACCTCTG CCTGGAAAGA AGGAAGGGGC
 351 ACCGATCGCT TCTGAGTTGG GGACAGGGCC ACACTTGGAC CTGATGAGTT
 401 CCAGGAGGCT GGCCCCAGCC TAGGGGCCTC CTGCACCCCC TTCCTAGCTC
 451 CTGGGTAGTG CCCCTCTTGC ATTTCCCTGC CGCTCCCCAG AAAGGGCTGG
 501 TTTCTGGGCA GGGAGTGTGG TGTCCGGGAC AATCTGCAGG TAGGGTGCAT
 551 CCTAGAAATC TCTGAGCTGC CACACCCAGA GAGAGGCCAG GACTCTTCTT
 601 GGCGTTCCTT GCCCTCTCTT CCTCCCCTAG GACTCCCCAC TCCCCACCTG
 651 CCTGTACTGG TTATGTAATT AACCCAGCTG AGTCTCTCTG CCATGCTGGT
 701 GGTAGTGGTG TCCAGGGATG CCTAAGGGGC TTCGGGACCT GGAGGGACAC
 751 ATGGGGAGGA GGGATAGGTA CTTCCCCCTA GTTGGGAGCC CATGTAAGTG
 801 TATAAACACC TGTTGGAGAA GGGACACTGC ATGGGGCAGG AAGGAGTTCA
 851 GGGTCCTAAT CTTAGTTAAC AACTCAACTG GCTATGAGGT CTTCACTTCC
 901 CTAAGTCACT GGGTTTGTTT TTTGGGGGGT TTGTTTGTTT TTTAAACCTT
 951 CAATAAAATG AGAAGAATCT CTCTCACGCA CACTGCATGC ATGTGAGCTC
1001 ATGCAACAGT AGATAGCAGC CCCTCCTGGG ATTGCTAGGA GGTTCCACTG
1051 CTAAGTTTGT GGGAAGCTTA GATGAATGAA TGACCCCTGC CCATAGCAGT
1101 GGTCACTGTT TATTGAACAC CTACTCTGGC CTAGGCACTG GGCTTTACAT
1151 GCACACATCA TAACACTTAA TAAAGTTTCT TGCCCAAGGT CACACTTCAG
1201 GTGAATGGCA GAGCTAGGAA TCAAGCCCTG GCGGTTCTCA TTCCACATCC
1251 TGACCTGTAT TTACTATGCT GTGTGCGCAC ATACCCCGTG GAGTGAGTCC
1301 TCTGAACCAG GACAACCTGG GGGACATTCA GCTGTGGCTT GTGCATATGT
1351 GGAAAGAACA TGCATCTGCA GAGAAGTATG CACCCATGCG GAAAAGCATG
1401 GCCTTGCCAG AATCCGGCGA ACCCACCTGC CCTGGAGCCA GTTAGCAAGT
1451 GCTGATGTCA CCCTCCTGGG AATCCAGACA GGAGGTCTCA GGCATGTAAC
1501 AGCCTCTCTG GTCACCATCA CCAACAAAAG AAGAAAGGTT CTCTCCTTTT
1551 CCTGGCTAAG AGATTTACTT GGATTTTCTC AGAAGTAGGG GCTGTTGACC
1601 TCATTTTACC TATGTGCAGA AGCATGGCTC CAGTTGAGAA GGTGATTTGC
1651 CCACTGACCT GCAGCAAGGA CACACCAGAG CTGATGAATT CGTATCAAGG
1701 CCCAAACCCC TAGCAGCCCT TTTCTGGGCA CCTGCTATGT GCCAGGCCCT
1751 CTGGGCTCTA GGGGATGCCA GAGAATCAGA CCCAGACCTT GGCCTATATG
1801 CATTCACTGG TTAGAATCAC TGAACTTGGC CAGGCGCGGT GACTCACGCC
1851 TGTAATCCCA GCACTTTGGG AGGCCAAGGT GGGTAGATCA CCTGAGGTCA
1901 GGGATTCCAG GCCAACATGG CGAAACCCCA TCTCTACTAA AAATACCAAA
1951 ATTATCTGGG TGTGGTGGCA GGTGCCTGTA ATCCCAGCTA CTCGGGAGGC
2001 TGAGGCAGGA AAATGGCTTG AACCCAGGAG GTGAAGGCTG CAGTGAGTCG
2051 AGATCATGCC ACTGTACTCC AGCCAACTTG AAAGTTGGAA GAAGTACTGC
2101 GACATCGTAG AAAGGAGTAG CTGCCCTTCG GGTTGTGATT GGGCACACTT
2151 CTTACTCCTT CTAAGCTTCT CTCTAAAGTG GAATAACAG TACTTATCCC
2201 TTAGAGATGT CGTACTGACC AAGGATAACC ATATGGGCAT GCCAGCAGAG
2251 TAAGTGCTCA GCAGTGTTGC ACCCCAGAGG CGACGTGGTC ATCTAGTGCA
2301 GCATTCTCAA CTAGGGCAT TTGGAAATGG GGGCAGGGGG AGTTTTTGGT
2351 CATCATGGTG TCTGGAGGCT GGCAGTTACC TCTTGGGGGC CACGGAAAGC
2401 AAATGTCCTG CAATGTGTGG GCAGTCCTGC ACAATCGAGT TCTCTCCCCA
2451 CAAAATGTCA GGAGTGCCAG CACTGAGACA CACCTGCCCA GTCCCACCCA
2501 TTCAGGAGGA CACAGACTCA GAGGTGTTGC CGTCTTGTCC CAGGCTCTGT
2551 GGGGAAGCTG GGATCAAACC AAGTCCAGTG CGCTTCCCAC TCTGCTCTGC
2601 AGCCTGTTTT GGTTGGAGTT GGACCTGGAG AAAAGTCAAG TCATAAGTCA
2651 AGAAAGATTG GGCCCTACTA CTGGAATGCA GGAAAAAATG GAGGAGGGAT
2701 GGAGAGGTTT TGGAAAGGCA GCCACAGGGG TTCTGGGAGA GGGAAGGCAT
2751 TCTAAGTGGC AGTAACAGCT TCAGCAAAGT CCCAAAGGTG GAAAAGTGCA
2801 GGACACGTCC AGGGATAAGC CAGTGCACTA AGCCCACCTC TTGTCCCCAC
2851 AGTCCAGGTG GAGGCCGCAG AGGGCCCAGG GCAAGCAGAG GCAGCAATGG
2901 TTGGTCCTGA CGGTGGCTGA GCCCCAGCC CCTGGAATAT GCAGCCCGGG
2951 GGAGCCCCAG ACAGCGGCAA GGACGAGGTG GCGGAGTGGG GCGGGAGGCA
3001 TGGTCTCCAC CTACCGGGTG GCCGTGCTGG GGGCGCGAGG TGTGGGCAAG
3051 AGTGCCATCG TGCGCCAGTT CTTGTACAAC GAGTTCAGCG AGGTCTGCGT
```

FIGURE 3A

```
3101 CCCCACCACC GCCCGCCGCC TTTACCTGCC TGCTGTCGTC ATGAACGGCC
3151 ACGTGCACGA CCTCCAGATC CTCGACTTTC CACCCATCAG CGCCTTCCCT
3201 GTCAATACGC TCCAGGTAGG AGGACCCTGG GGGGCATGGG TTAGTGGGGA
3251 AACGGATGGG TAGGGGAGAG GCTGGATTCC AAACTGCTGT AGCTTGGGCC
3301 CTATTGCCAG GGCCCCATCA CTGAGTTTGG GAGCTCCACA CTGCACCTTG
3351 GGCCACTCTG CTTAGAGCCG TTCCAGGAAT CCATTCATTG GTGTGCTAGT
3401 TTATTCAACA AATATTTGGT GACCGTTCAA TGTGTGCCAG GCCCTGCAGT
3451 GGGCACTGGT GCAGAATGGT GAGCAAAAAA TATATGGAAT TTGCTTTCAA
3501 GAAACTCATA GTCTGGTGAG AAAAGGCAAA TATGGTGTGA TAAGTTCTAT
3551 GATTGGAGGA GCAGGGAGCT GGGGCAGCCC TTAAGGGGGC ATCTAGGCCA
3601 TCCAGATGTG TTGGGGTGGA GTTGGGGGGT CACAGAGGGT GATGTCTCAA
3651 CTAAATAGGT TTTAGGCAGG TAAGAGTCAG TAGAGAAAAG GACAGGGAAC
3701 ACTAGGCTAC TGTGAGTATT CGGAGCTGTG CCTACCGTAA CCTCACTCCA
3751 CATCCTCTGG AGAAGGGACA GCAGCAGAAC AGACGGGGCC CTGGGAAAGG
3801 TGTGTTCTTG GAGACTCTGG AGACCCCAGT CAGGTCTCTT GCCCAAGGCC
3851 CTCTTCTCTT AAGTGATGCT CTGCCCCTGA CCTCAGGACC TGCCTGCTGG
3901 GCACCCTCCC TGCCAGGTTT GGATTTAAAT GCCTGAGGGT CCTCACTTAT
3951 TGTGTTCCTT CCCCACTGCC TGCTGGAACC AGGTCCTCTT GCCCTCTCTC
4001 AACCTCTGAC TTGAGAGGGA GTGGAGAGAA AAAGGAAGCT GAGCTCTAGG
4051 ACATGTTTGC TCACTGAAGG AAGCCTCTGA CCAGAGTGTA CAGAGCTTTT
4101 CCAGGAAGGA CAGGCACAGT GGTGGAGGCC CAGAAGACAG GGACAAGGC
4151 TCGTCCAGGT GTAACTGAGC AAATCAAGCA GTCTCTCAGG CTGAGACCCT
4201 GGGCTGGGAG ATGGCGGGCA GCTCAGCACT CAGCACTCTC GGCAACACCA
4251 GGCAGGAGGG CCCTGGCCTA ATCTGCCGGA GACACCTGTT CACCCATCCC
4301 AGGCACCTGG GGTCAGGAGG AAAGATGGAA GCCTGATCCC GCATCTGCCC
4351 TGGAAGCAGT GAGGCTGAGC CTGTCAGGGC AGACAGTCTG GATGCAGGGC
4401 CTTCTAGTTC TCTTCTAAAG GAGACTTTAA CAATCACCTG ATTGGACATT
4451 CAAATCTTGC TCCAAGCCTA CACACTGAGC TTTGTTGATT TCATCTTGCC
4501 CCCTTTACCT TGATTCCTGC CCCACTCTCT ATAACCACTC TTATCGAATT
4551 TTTCTTTCTT TTTTAAAATT TATTTATTTT TTTATTTTAG ATGGAGTCTC
4601 CCTCTGTCGC CCAGGCTGGA GTGCAGTGGC ACGATCTCGG CTCACTGCAA
4651 TCTTCGCCTC CCGGGTTCAA GCGATTCTCC TGCCTCAGCC TCCTGAGTAG
4701 CTGGATTACA GGCACCTGCG ACCACACCCA GCTAATTTTT GTATTTTTAG
4751 TAGAGATGGG GTTTCACCAT GTTGGCCAGG CTGGTCTCAA ACTCCTGACC
4801 TCAAGTGATC CGCCTGCCTA GGCCTCCCAA AGTACTGGGA TTATAGGCAT
4851 GAGCCACCAC GCCTGGTCTC TTATCCATAC TTTCAGTGTT TCTTTACCCA
4901 AGTAAGAAAA TGCATTCTTC CCTGCTTCTT ACGTAAAGAA CAAAACAAAA
4951 ACAAGAACCA TACTGTTCTG TACCTTGATT TTATTTTATT TTTAAAATTT
5001 TTTGTATAGA TGGGTCTTGC TGTGTTACCT AAGCTGATCT CGAACTACTG
5051 GCCTCAAGCG ATCCTCCTGC TTTGGCCTCT CAAAGTGCTG GGATTACAAG
5101 TGTGAGCCAC TGTGCTTGGC GCTGTACCTC AATTTTTTTA ACTTGCTATT
5151 ATAACCTGAA GATTTTTCCA GGCCATTATC TAGAGGACGT CCTCATTCTT
5201 TTTTCATGGC CACGCCCTAC TCCATTGAAG AGCTATACCA TGGAGTCCTT
5251 TCTTGTTGGA TAAGTGGGTG GTATCCAGTC TTGTGCTGTT TCAAACAGTG
5301 CCACAATGAG TGGCCTTGTA GATAGGTCAT TTTGAACATA AGTAGGTATA
5351 TCTGTGGGAT CAATTACCGG AAAGGGCATT GCTGGAAATG GCACTGCTGG
5401 ATCACAATGC CTGGAAATGG CATTGTGAAT ACAGAGCCAG GTGAGGTGGC
5451 TCATGCCTAT AATCCCAACA CTTTGAGAGG CTGAGGCAGG CGGATCACTT
5501 GAGCTCAGGA GTTCGAGACC AGCCTGGGCA ACATGACAAA ACTCCGTCTC
5551 TACCAAAAAT ACAAAAAATT AGCCAGGCAT GGTGCTCCAT GCCTGTGGTC
5601 CCAGCTGCTT GGGAGGCTGA GGTGGAGAA TCGCCTGAGG CCGGAGGGTT
5651 GAGGCTGCAG TGAGCTGAGA GTGCCACTGC ACTCCAACTT GGGTGACAGA
5701 GTGAGGCCCT GTCTCAAAAA AAAAAAAAA AAAGTGTGAC TGTAACTGGA
5751 GTTTGGAGGG GAGGTTATTT CCAGATTGCC CTCCATAGCA GTGGCGTATG
5801 CTGTGCTCCT GTGAGCAATG TATATGAGAG CCCGTTTTCC TACAGTCTTG
5851 CCATCAGAGT ATATTGTCAA ACTTTGACA ATATATTTGA CAATCTGAGA
5901 GATGAGATAT GATATTCTCC TTGTAGTCTC CATTTGCATC TCTGATCGTG
5951 GGTGAAATTG AGCATCTTTC ATAGGTTTAA GGGCTTTGT GTTTCTCTTT
6001 TCAAGAACTA TTGATGTCCT TTGCCCATTT TTCTATTGGG TTGTTGGCTT
6051 TTTTCTTCTT GACTGACCCT GAGTTTTGGA CTCTAAGATA TCCAAGATTT
6101 CACTCCTGGA GCCCAGTAAG GGACTTTTGG CAGAGAAATA CTGTGAAAAA
6151 GGTATCCTCA AGGCACCAAA GATTAAGTAT AAAACCTAAG AATCCTGATG
```

FIGURE 3B

```
6201 GCCACCATCT GGAAACAAAA TAATACATTC TTCTCCAATG CCAGATGAGA
6251 TAGAGCCCAG GAGAGTAGTG TTTCCTGGGT GTGAGCCTCA GTGTCTTCTG
6301 CAGCCCCTTC TATCAGAGAA GGAAGCTGAG ATTATCAGGT GCTTGCAACT
6351 CACCAAAGGA ATTATCAGCA AATGCATGGT TGAGATGCAG GTGGCTGAGC
6401 CTTGTCCCTG AAACTGGACT CCCTTTCTAT TGCTCCTTCT CTGTCTTGAC
6451 AGAGCCCCAA GATGGCCTTT TACAGTTTGG AACCCTGCTT CCTCCCTTCA
6501 ATCAAGGGGG AAGGGATAAG CTAGCCAATC AGGGGCCTTC CTCCTCTCTC
6551 TTTTAGGAAC CCCCAGAGAG GAGTGGGTGG GAGGAAGCCA GGAGTTCCCC
6601 TCAAGGAGGC AACATGTTGG GGGAGAGGTG GGGCTGTCAC CCTCAAAAGC
6651 TGGCAGCTGC TCCCTCTCCC CAGCAGACAG CTTGAAGAGA CTGGGAGCTT
6701 CTCATCCCTC CCACTTCTCA CTGATCTCCA TTGGTCTTGG GGGATCGTGG
6751 GAGCATCCGT ATACACAGGT TCCAGGCTCC TGGAGATCAC TGTGTCCAGC
6801 AGAATGCAGT CTTCCCTGGC CTAAGAAACC AGTTTCCTAT GGTTTTAGGT
6851 TTGTCCTCGG CATCCTCCCG CCGCACCAAA AATTTAAACC TCAGCACAAA
6901 GAAAAGATGC CACATCATCT CCCTAGGGAA ATCCACTGCA GCATCTTCTA
6951 AGCCTTTGAG TTGGGAAGTG CTGTTCTGAA GTTGGACTTA ACTCTGCACT
7001 ACTGCCACCA AAGTCGTTTC CTTTTGATCC TTCTTGGAAG TGGAGAACTG
7051 TAGTCCTCCT TTGTGCCTGG CCCCTGCCCC ACTCAATTCA GATGCTGGGA
7101 CAGGAGACAT ACCTCCACCT TCTTCTAGTC TTTTGCCTGG GCTTTGGTGG
7151 GAGAAGACTC TGGTTTCCTT TGTCCTTGGA GGCCTCTGTC CCCCCACCTT
7201 TAGGGACCCC CTTCTTTCCA CACACTGGCT GCCTGAAACC GCTCTTGCAG
7251 CTGGCACGTT GACTAATGAA TCTGTTAAGG AAACTTCTCT TTAGTGTACT
7301 TGGCCTTTCT AGGAGTCTCT TCACCTTGAG CTGTACCCCC CAATCCCTTG
7351 AGAAGTTGCC ACAAACATTC AGGAAGTTCA TCTCCCTGGA GCTGCCCAGG
7401 GGCCCTACTC TACATCAGCC CATTATGCAT CCAGTCTGAA TCTTTTTCTG
7451 TTTCTCAACC CTGAGGGCAG AGAGAAGCAT ACAGAAGGGG CACATCAGGT
7501 AGCAGTCTAA GGGCAGTGGC AGAGGCAGGA GTTGCATTGA TCCCAGCTTG
7551 GGCCATGGAG AGCTCACCAG CCCAGGTAGT GCTATTAAGG AGCACCTGCT
7601 TTGAGCCAAC AGTGCTAGAC ACTCAGGGAG GAAGAGGGAG TATATACAAA
7651 TGAGGATGGC CTGGCTGTGG CCTTCTCAGG AGCTCACAGC AGAAGTGGGG
7701 AACTGGAGAT GGAACAGCTC TAATGAAAGT GTAATAGAAG GATTGTTAGA
7751 ACACAGGAGA TGAAGGGAGT AGTCCCCTGC TTGCAGGAAG GATGGGAAAT
7801 CAGGAAGCTT CTTGGAGGTG GTGGCACTTT AGCTGAACCT TGGAAGATAG
7851 AATTTTAACA GGTCCAACAC CCAGCTCAGA GCTGGACTCT TAGAGGTACT
7901 TAATAAATGT ACTTGTTGAA CAAAGGCCTC GATGGATGGA TGAGGGCACG
7951 ACATGGAGCA AGGCAGAGCT AAACTCCAGA TGTGCACAAG ACAGTGCAGT
8001 GGCCCTGTAG ATCAAACAAT GTGACCTGCT CCATCCTGGC TTGGGAATGG
8051 GGAGGCTACA GCTCCTCCAT TCTCCCTGGG CCTGGTCTCC TGGGGATGGT
8101 CGGGTATGGA AGGCTTCAGG TGCAGTGGCA GGTGAGAGCA CTGCCCCTCT
8151 GATGGGAGGT GTTTGGGGGC TAGGGGAGCC CTCATGGCTG CTCTGACCCT
8201 GGTACTGGCT GGGGATATTG CAGGAGTGGG CAGACACCTG CTGCAGGGGA
8251 CTCCGGAGTG TCCACGCCTA CATCCTGGTC TACGACATCT GCTGCTTTGA
8301 CAGCTTTGAG TACGTCAAGA CCATCCGCCA GCAGATCCTG GAGACGAGGT
8351 GAGAGGCTGG AACACAGTCC ATTGCCACCT CTGTGGATGC CCCAGTGCTA
8401 GCCAGTCCCT GTGAAAAGGG CACAGTATAG GGACACAGAT AGAGGTATAT
8451 GTGTTCTAAG ATTTCCACAC ATACACTCAA ACATGCATAC ATTGTGCTGT
8501 TCCCATTTCT GTCAACTCAT GTTGGGACCG TGGCTGTGGG GGTGGCTAGA
8551 GTAGTGCAGT AGTTAAGAAC TGGGACTTCT GGAACAAGAC TTCCAGGGCC
8601 ACTCAGCTGC ATGACTTGAA GCCAGTAAAC ATTTAAGCCT ATGTCCTCAT
8651 CTGTAAAATG GGGATAACAG TAGAACCCAT CTTTTAGATC AGTTGTGCTG
8701 ATCAGAGAAT ATAACACCTC CAGGGCTTAG GGCTGCGCCT GGAGCAGAAC
8751 CTACGGTGGT GGTAGTATTG GCCAGGCACA GCCTGCCCTG CTGGGAGTAC
8801 AGCGGTTGTG GGCTGACAG AGTTCTGAGC TGCCTGCCTC GCCCCACAGG
8851 GTGATCGGAA CCTCAGAGAC GCCCATCATC ATCGTGGGCA ACAAGCGGGA
8901 CCTGCAGCGC GGACGCGTGA TCCCGCGCTG GAACGTGTCG CACCTGGTAC
8951 GCAAGACCTG GAAGTGCGGC TACGTGGAAT GCTCGGCCAA GTACAACTGG
9001 CACATCCTGC TGCTCTTCAG CGAGCTGCTC AAGAGCGTCG GCTGCGCCCG
9051 TTGCAAGCAC GTGCACGCTG CCCTGCGCTT CCAGGGCGCG CTGCGCCGCA
9101 ACCGCTGCGC CATCATGTGA CGCCTGCGCG CCCCTCGGGC TGCACCGGCA
9151 CTGGCCGAGC GGAGGGCGGG GCCGTACTGC GGGGCTGGGG CGGGGAGCGG
9201 GCGGGAAATG GAACTGTGAC GGTCCCGGCC TGAGGCCCCT GCAGCCACGC
9251 ACCTCCCGGT GAGAAGCAGA GCGCGAGAGG GAGCCCTCCG TAACTGCCCA
```

FIGURE 3C

```
 9301 GCCCTGCCCC TTGCCCCCGT GGCTTCCTGG GACAGCCGCC TTCAGTGCTG
 9351 TATTTAGTGC AGTGCCCGGC CCGACCCGCG GGGGTGCCAC AGCCTTTTGG
 9401 GATGGGGGTG AGCGTGCAAT GGAGGCTGGG GGTGGCGAGG TGCCGCCTTG
 9451 GCCGGGCCCC CACGTGTCTT CTCCAGAATG TGTCTGTCTT TGCCTGGTGT
 9501 CTTCCTTTCC CGTGTCCGCC CACCCCAGCG TCTGTTGGTA CTTACCTGTC
 9551 TCACCTACCC TCCAGTCCCC TCCCAGCTCC GCTCACAGGG CTCTCATTTC
 9601 GTCCATCCCC TTGTCGCAGA TCCTGGCAGC TTCTTTGTGA GGCCAGGCCT
 9651 TCTGACTGTC AGCACCACCG GCACAGGGCA GAGATGCGGG TGGCCCAAGG
 9701 ACCACGATCA AGGGGTCCGG GGGACCGAGG TCCCAGATCA GTGAGGGGAG
 9751 AAGGTTGAGC TCTCCGGCTT CCAGGGAGAC CTCCCCGCCC AGCAGCCCCC
 9801 AGAGACACAA CAACCTACCT TCCAGCCTTA ACTCGATGGT CCGTCCCTGC
 9851 CAGGTGCCCC TCACTCTTCC TGACCCCAAA GCCAGATCAC CCCCTGGGTT
 9901 AAAACTTTTT TTCTTTTTTT TTTTTGGACA GAGTGTGGAA AGGGAGCCCC
 9951 CCAAAGGATA GCTTCTTTTT CATGATGCCA GGCTCCAGTC CTTTATTCCC
10001 TTCTGCATAC TGCAATCTGA TCTGTCAGAC TGGGGAATGT TGGGTTCTGG
10051 GGTCTGGTCG TGGGCAGGAT GGTGCCCAGA AGGGGGTTAG GTTGTCCCAG
10101 TGAAAATTCT GTTGCCCCGT CTCAACCCCA TCTGACTACC CCAGACTCTG
10151 CCTGCCTCAG ATCTCAGACT ATCCTGATTA ATCTGGGGAA GAACAGAGCC
10201 AGGGAAAGAA TGGTGGGGAC CCCTGTACTT GGGGAGACA CACCTGCATC
10251 TTCCTCCTGC CACAGATGGA GGCCCTCAGG ATCTGACACC CTCTTGTCCC
10301 AACACCAGTC AGCCCTATAC CCTAACTCAC TCCACCCCAT TTTCTCCGGC
10351 TGCCTGGCCG GGTTTCTACC TCTCGTCACC GGAGCTGATC ACTGTCAGTT
10401 TTGTACCGAT TTAGAAATAA CAATAATAAT GAAGATTCTA GGAATGGCAT
10451 GAGGGATTGA TGGGGGACTT GGAGGGAGGG ACAAGTGGTG CCCTGTCCCC
10501 TGCTCCCCTG GCCAAAGAAA GCTGTCCTTG AGGCTGAGCC CTCAGCCCTG
10551 GCCTGGTGGG GGGACAGCAA GGTCCCTTGT TATAAGAGGG GCAGAGAGGA
10601 CAACTCCGCT TTGGCCAACC TAGCCAAGGC TGCAGCATAT AGACCAGGAA
10651 ATCAGGTAGC CCAGACTGGT GATGGAGCAG AGTCTGGGGG AAGGGTCGTG
10701 GGTGGGGAAT TTATCACCAA CATCCATTGT AGGGGGAATC TATGATTCTG
10751 CTTCCCCAGC GGATTCCCAC TCTGTCCACC AAGTGGGGGG TAGCACAGCC
10801 TCACAGCAAC CGCCCTGACC TTGGGCAGTC TAGTGTTCCT GCATTCTAGT
10851 CCCTGCTGTG CTGCAGGACT TTGGGCAAGT GACCTGCCCT CTGTGAGCCT
10901 CCCTCTGACA CAGAGGAGGT GGCTCCCCTT CCCCACACCT TAGAGTGGCT
10951 GGGAGGGTAA CAAAGAGGGC CTGCCCCTTT AGTCTCCTGC ACCCCTGCCC
11001 CCTGGTTCAC CAGAGGGAGC GGATGAAGGA TGGCAGCATC TCACATGCCC
11051 CATCACCAAC TCTGAGGCAC CTGGGGTGGG GGGGCGGAGC CCAGGCCTCT
11101 GGCTGCTCCC CTGTGGGAGC CATTGGAATG TATCCCCTGA CAGGCCCCCT
11151 TCCGCCTCCA CCTCAACCCA GGTCTTGGAT TTCAGGTCCC TCCACCCCCA
11201 TTCTGAGTCT CTGTCCTTCT CCTTCCACCC GCTCCCAGGG TTTCCCACCA
11251 CAGGGTCTGG AAGTGTGTGT GACGCCCATT GAGCTGTTAC CCGAAGTCAG
11301 ATTAAAAATC AGGGAGTGTT TTCCCTCGTT TCTGTACCAA GGTGTTGGCT
11351 CCATTCCTCA TGGTAGGAGG GGAGGGGTCC CCACAGGGCT TGCCTGCTGA
11401 GCTCCGTGTG GAAGGAGGGT GAAGGTGGTG AGGTGGCCCC CAGTCCCAAA
11451 GCCCAGGTCA ACAGGGAGAC CACCGGTGAA GAGTTTGGGA TTTATCACCT
11501 TTCCACCTAA CCCCAAACCC TCCAGCTAAT TCCAACCATT CAGAAGGGAA
11551 GCAGAACTTC TCCCCTGCCA CTGTCTGGAA AATTTCCATA ATGGGACTCA
11601 ATCCCAGCTT CTCCGTCTGC GTCTCGTCCT TCCCACTCAA GGCTGAGACT
11651 TTACAGCCTC TCAGTCATAA CTTCTTGGAT GTAGATGTGT TAGGAACACT
11701 TTCAGCCACC CGTCTTGTCC CTGAGTGATC TCAGGTCCCA AACTCCAGAG
11751 CAAAGCTTTG AAATCTTGGG CAAGGGTGCC TTGTGGGAGC CTGTGTGTTG
11801 AGGGCAGGAC TGGTCTCTGT CCGTGGTGCT GACCCACCAG CCACTTCCAG
11851 GAAAGATGGG GCTGCCTGGC AAGGTTGGCT GAGCCTCAAA AGAGGAAGCC
11901 TCTCTCACCA CCAACTCCTT CCTTCTAGTC CCCATCTCCT CCAGTGGGAT
11951 AACATCTGAA GCTATACCTC CCCGCACCAC CACAGTCCTG GAGTGAGGGA
12001 CTCAAGAAGC TGGGGGGCAG GGGGAGGCAG GTTCAGTGGT TCACATCTTT
12051 AATCCCACTG CTTTGGGAGG CCAAGGCAGG AGGATCGCTT GAGGCCAGCC
12101 TGGACAACAT AGTAAGAC    (SEQ ID NO:3)
```

FEATURES:
Start: 3000
Exon: 3000-3215
Intron: 3216-8223

FIGURE 3D

Exon: 8224-8348
Intron: 8349-8849
Exon: 8850-9117
Stop: 9118

CHROMOSOME MAP POSITION:
Chromosome 17

ALLELIC VARIANTS (SNPs):
DNA

| Position | Major | Minor | Domain |
|---|---|---|---|
| 2455 | A | C | Beyond ORF(5') |
| 2785 | A | G | Beyond ORF(5') |
| 3482 | T | A | Intron |
| 6189 | A | G | Intron |
| 6491 | T | C | Intron |
| 7353 | A | T | Intron |
| 8688 | A | G | Intron |
| 10789 | G | C | Beyond ORF(3') |
| 11079 | G | A | Beyond ORF(3') |
| 12087 | A | G | Beyond ORF(3') |

Context:

DNA
Position

2455
CTCCTTCTAAGCTTCTCTCTAAAGTGGGAATAACAGTACTTATCCCTTAGAGATGTCGTA
CTGACCAAGGATAACCATATGGGCATGCCAGCAGAGTAAGTGCTCAGCAGTGTTGCACCC
CAGAGGCGACGTGGTCATCTAGTGCAGCATTCTCAACTAGGGGCATTTGGAAATGGGGGC
AGGGGGAGTTTTTGGTCATCATGGTGTCTGGAGGCTGGCAGTTACCTCTTGGGGGCCACG
GAAAGCAAATGTCCTGCAATGTGTGGGCAGTCCTGCACAATCGAGTTCTCTCCCCACAAA
[A,C]
TGTCAGGAGTGCCAGCACTGAGACACACCTGCCCAGTCCCACCCATTCAGGAGGACACAG
ACTCAGAGGTGTTGCCGTCTTGTCCCAGGCTCTGTGGGGAAGCTGGGATCAAACCAAGTC
CAGTGCGCTTCCCACTCTGCTCTGCAGCCTGTTTTGGTTGGAGTTGGACCTGGAGAAAAG
TCAAGTCATAAGTCAAGAAAGATTGGGCCCTACTACTGGAATGCAGGAAAAAATGGAGGA
GGGATGGAGAGGTTTTGGAAAGGCAGCCACAGGGGTTCTGGGAGAGGGAAGGCATTCTAA
(SEQ ID NO:11)

2785
TGCCCAGTCCCACCCATTCAGGAGGACACAGACTCAGAGGTGTTGCCGTCTTGTCCCAGG
CTCTGTGGGGAAGCTGGGATCAAACCAAGTCCAGTGCGCTTCCCACTCTGCTCTGCAGCC
TGTTTTGGTTGGAGTTGGACCTGGAGAAAAGTCAAGTCATAAGTCAAGAAAGATTGGGCC
CTACTACTGGAATGCAGGAAAAAATGGAGGAGGGATGGAGAGGTTTTGGAAAGGCAGCCA
CAGGGGTTCTGGGAGAGGGAAGGCATTCTAAGTGGCAGTAACAGCTTCAGCAAAGTCCCA
[A,G]
AGGTGGAAAAGTGCAGGACACGTCCAGGGATAAGCCAGTGCACTAAGCCCACCTCTTGTC
CCCACAGTCCAGGTGGAGGCCGCAGAGGGCCCAGGGCAAGCAGAGGCAGCAATGGTTGGT
CCTGACGGTGGCTGAGCCCCCAGCCCCTGGAATATGCAGCCCGGGGGAGCCCCAGACAGC
GGCAAGGACGAGGTGGCGGAGTGGGCGGGAGGCATGGTCTCCACCTACCGGGTGGCCGT
GCTGGGGGCGCGAGGTGTGGGCAAGAGTGCCATCGTGCGCCAGTTCTTGTACAACGAGTT
(SEQ ID NO:12)

3482
ACCCATCAGCGCCTTCCCTGTCAATACGCTCCAGGTAGGAGGACCCTGGGGGGCATGGGT
TAGTGGGAAACGGATGGGTAGGGGAGAGGCTGGATTCCAAACTGCTGTAGCTTGGGCCC
TATTGCCAGGGCCCCATCACTGAGTTTGGGAGCTCCACACTGCACCTTGGGCCACTCTGC
TTAGAGCCGTTCCAGGAATCCATTCATTGGTGTGCTAGTTTATTCAACAAATATTTGGTG
ACCGTTCAATGTGTGCCAGGCCCTGCAGTGGGCACTGGTGCAGAATGGTGAGCAAAAAAT
[T,A]
TATGGAATTTGCTTTCAAGAAACTCATAGTCTGGTGAGAAAAGGCAAATATGGTGTGATA
AGTTCTATGATTGGAGGAGCAGGGAGCTGGGCAGCCCTTAAGGGGGCATCTAGGCCATC
CAGATGTGTTGGGGTGGAGTTGGGGGGTCACAGAGGGTGATGTCTCAACTAAATAGGTTT

FIGURE 3E

```
        TAGGCAGGTAAGAGTCAGTAGAGAAAAGGACAGGGAACACTAGGCTACTGTGAGTATTCG
        GAGCTGTGCCTACCGTAACCTCACTCCACATCCTCTGGAGAAGGGACAGCAGCAGAACAG
        (SEQ ID NO:13)

6189    GACAATCTGAGAGATGAGATATGATATTCTCCTTGTAGTCTCCATTTGCATCTCTGATCG
        TGGGTGAAATTGAGCATCTTTCATAGGTTTAAGGGCCTTTGTGTTTCTCTTTTCAAGAAC
        TATTGATGTCCTTTGCCCATTTTTCTATTGGGTTGTTGGCTTTTTTCTTCTTGACTGACC
        CTGAGTTTTGGACTCTAAGATATCCAAGATTTCACTCCTGGAGCCCAGTAAGGGACTTTT
        GGCAGAGAAATACTGTGAAAAAGGTATCCTCAAGGCACCAAAGATTAAGTATAAAACCTA
        [A,G]
        GAATCCTGATGGCCACCATCTGGAAACAAAATAATACATTCTTCTCCAATGCCAGATGAG
        ATAGAGCCCAGGAGAGTAGTGTTTCCTGGGTGTGAGCCTCAGTGTCTTCTGCAGCCCCTT
        CTATCAGAGAAGGAAGCTGAGATTATCAGGTGCTTGCAACTCACCAAAGGAATTATCAGC
        AAATGCATGGTTGAGATGCAGGTGGCTGAGCCTTGTCCCTGAAACTGGACTCCCTTTCTA
        TTGCTCCTTCTCTGTCTTGACAGAGCCCCAAGATGGCCTTTTACAGTTTGGAACCCTGCT
        (SEQ ID NO:14)

6491    AATCCTGATGGCCACCATCTGGAAACAAAATAATACATTCTTCTCCAATGCCAGATGAGA
        TAGAGCCCAGGAGAGTAGTGTTTCCTGGGTGTGAGCCTCAGTGTCTTCTGCAGCCCCTTC
        TATCAGAGAAGGAAGCTGAGATTATCAGGTGCTTGCAACTCACCAAAGGAATTATCAGCA
        AATGCATGGTTGAGATGCAGGTGGCTGAGCCTTGTCCCTGAAACTGGACTCCCTTTCTAT
        TGCTCCTTCTCTGTCTTGACAGAGCCCCAAGATGGCCTTTTACAGTTTGGAACCCTGCTT
        [T,C]
        CTCCCTTCAATCAAGGGGGAAGGGATAAGCTAGCCAATCAGGGGCCTTCCTCCTCTCTCT
        TTTAGGAACCCCCAGAGAGGAGTGGGTGGGAGGAAGCCAGGAGTTCCCCTCAAGGAGGCA
        ACATGTTGGGGGAGAGGTGGGGCTGTCACCCTCAAAAGCTGGCAGCTGCTCCCTCTCCCC
        AGCAGACAGCTTGAAGAGACTGGGAGCTTCTCATCCCTCCCACTTCTCACTGATCTCCAT
        TGGTCTTGGGGGATCGTGGGAGCATCCGTATACACAGGTTCCAGGCTCCTGGAGATCACT
        (SEQ ID NO:15)

7353    GTCCTCCTTTGTGCCTGGCCCCTGCCCCACTCAATTCAGATGCTGGGACAGGAGACATAC
        CTCCACCTTCTTCTAGTCTTTTGCCTGGGCTTTGGTGGGAGAAGACTCTGGTTTCCTTTG
        TCCTTGGAGGCCTCTGTCCCCCCACCTTTAGGGACCCCCTTCTTTCCACACACTGGCTGC
        CTGAAACCGCTCTTGCAGCTGGCACGTTGACTAATGAATCTGTTAAGGAAACTTCTCTTT
        AGTGTACTTGGCCTTTCTAGGAGTCTCTTCACCTTGAGCTGTACCCCCCAATCCCTTGAG
        [A,T]
        AGTTGCCACAAACATTCAGGAAGTTCATCTCCCTGGAGCTGCCCAGGGGCCCTACTCTAC
        ATCAGCCCATTATGCATCCAGTCTGAATCTTTTTCTGTTTCTCAACCCTGAGGGCAGAGA
        GAAGCATACAGAAGGGGCACATCAGGTAGCAGTCTAAGGGCAGTGGCAGAGGCAGGAGTT
        GCATTGATCCCAGCTTGGGCCATGGAGAGCTCACCAGCCCAGGTAGTGCTATTAAGGAGC
        ACCTGCTTTGAGCCAACAGTGCTAGACACTCAGGGAGGAAGAGGGAGTATATACAAATGA
        (SEQ ID NO:16)

8688    TGCCCCAGTGCTAGCCAGTCCCTGTGAAAAGGGCACAGTATAGGGACACAGATAGAGGTA
        TATGTGTTCTAAGATTTCCACACATACACTCAAACATGCATACATTGTGCTGTTCCCATT
        TCTGTCAACTCATGTTGGGACCGTGGCTGTGGGGGTGGCTAGAGTAGTGCAGTAGTTAAG
        AACTGGGACTTCTGGAACAAGACTTCCAGGGCCACTCAGCTGCATGACTTGAAGCCAGTA
        AACATTTAAGCCTATGTCCTCATCTGTAAAATGGGGATAACAGTAGAACCCATCTTTTAG
        [A,G]
        TCAGTTGTGTGCTGATCAGAGAATATAACACCTCCAGGGCTTAGGGCTGCGCCTGGAGCAGA
        ACCTACGGTGGTGGTAGTATTGGCCAGGCACAGCCTGCCCTGCTGGGAGTACAGCGGTTG
        TGGGGCTGACAGAGTTCTGAGCTGCCTGCCTCGCCCCACAGGGTGATCGGAACCTCAGAG
        ACGCCCATCATCATCGTGGGCAACAAGCGGGACCTGCAGCGCGGACGCGTGATCCCGCGC
        TGGAACGTGTCGCACCTGGTACGCAAGACCTGGAAGTGCGGCTACGTGGAATGCTCGGCC
        (SEQ ID NO:17)

10789   TGCCCTGTCCCCTGCTCCCCTGGCCAAAGAAAGCTGTCCTTGAGGCTGAGCCCTCAGCCC
        TGGCCTGGTGGGGGGACAGCAAGGTCCCTTGTTATAAGAGGGGCAGAGAGGACAACTCCG
        CTTTGGCCAACCTAGCCAAGGCTGCAGCATATAGACCAGGAAATCAGGTAGCCCAGACTG
        GTGATGGAGCAGAGTCTGGGGGAAGGGTCGTGGGTGGGGAATTTATCACCAACATCCATT
        GTAGGGGGAATCTATGATTCTGCTTCCCCAGCGGATTCCCACTCTGTCCACCAAGTGGGG
        [G,C]
```

FIGURE 3F

```
        GTAGCACAGCCTCACAGCAACCGCCCTGACCTTGGGCAGTCTAGTGTTCCTGCATTCTAG
        TCCCTGCTGTGCTGCAGGACTTTGGGCAAGTGACCTGCCCTCTGTGAGCCTCCCTCTGAC
        ACAGAGGAGGTGGCTCCCCTTCCCCACACCTTAGAGTGGCTGGGAGGGTAACAAAGAGGG
        CCTGCCCCTTTAGTCTCCTGCACCCCTGCCCCCTGGTTCACCAGAGGGAGCGGATGAAGG
        ATGGCAGCATCTCACATGCCCCATCACCAACTCTGAGGCACCTGGGGTGGGGGGCGGAG
        (SEQ ID NO:18)

11079   CCAAGTGGGGGGTAGCACAGCCTCACAGCAACCGCCCTGACCTTGGGCAGTCTAGTGTTC
        CTGCATTCTAGTCCCTGCTGTGCTGCAGGACTTTGGGCAAGTGACCTGCCCTCTGTGAGC
        CTCCCTCTGACACAGAGGAGGTGGCTCCCCTTCCCCACACCTTAGAGTGGCTGGGAGGGT
        AACAAAGAGGGCCTGCCCCTTTAGTCTCCTGCACCCCTGCCCCCTGGTTCACCAGAGGGA
        GCGGATGAAGGATGGCAGCATCTCACATGCCCCATCACCAACTCTGAGGCACCTGGGGTG
        [G,A]
        GGGGGCGGAGCCCAGGCCTCTGGCTGCTCCCCTGTGGGAGCCATTGGAATGTATCCCCTG
        ACAGGCCCCCTTCCGCCTCCACCTCAACCCAGGTCTTGGATTTCAGGTCCCTCCACCCCC
        ATTCTGAGTCTCTGTCCTTCTCCTTCCACCCGCTCCCAGGGTTTCCCACCACAGGGTCTG
        GAAGTGTGTGTGACGCCCATTGAGCTGTTACCCGAAGTCAGATTAAAAATCAGGGAGTGT
        TTTCCCTCGTTTCTGTACCAAGGTGTTGGCTCCATTCCTCATGGTAGGAGGGGAGGGGTC
        (SEQ ID NO:19)

12087   GAGCCTGTGTGTTGAGGGCAGGACTGGTCTCTGTCCGTGGTGCTGACCCACCAGCCACTT
        CCAGGAAAGATGGGGCTGCCTGGCAAGGTTGGCTGAGCCTCAAAAGAGGAAGCCTCTCTC
        ACCACCAACTCCTTCCTTCTAGTCCCCATCTCCTCCAGTGGGATAACATCTGAAGCTATA
        CCTCCCCGCACCACCACAGTCCTGGAGTGAGGGACTCAAGAAGCTGGGGGGCAGGGGGAG
        GCAGGTTCAGTGGTTCACATCTTTAATCCCACTGCTTTGGGAGGCCAAGGCAGGAGGATC
        [A,G]
        CTTGAGGCCAGCCTGGACAACATAGTAAGAC    (SEQ ID NO:20)
```

FIGURE 3G

ISOLATED HUMAN RAS-LIKE PROTEINS, NUCLEIC ACID MOLECULES ENCODING THESE HUMAN RAS-LIKE PROTEINS, AND USES THEREOF

FIELD OF THE INVENTION

The present invention is in the field of Ras-like proteins that are related to the RRP22 subfamily, recombinant DNA molecules and protein production. The present invention specifically provides novel Ras-like protein polypeptides and proteins and nucleic acid molecules encoding such peptide and protein molecules, all of which are useful in the development of human therapeutics and diagnostic compositions and methods.

BACKGROUND OF THE INVENTION

The novel human protein, and encoding gene, provided by the present invention is related to the Ras-like protein family. The protein of the present invention shows the highest degree of similarity to the RRP22 gene, which is found on chromosome 22. RRP22 defines a subgroup within the Ras-like protein family (Zucman-Rossi et al., *Genomics* 38 (3), 247–254 (1996)). The gene encoding the Ras-like protein of the present invention is found on chromosome 17. It has been suggested that growth-arrest-specific and Ras-related genes may be involved in tumorigenic processes (Zucman-Rossi et al., *Genomics* 38 (3), 247–254 (1996)).

Ras-like proteins, particularly members of the RRP22 subfamilies, are a major target for drug action and development. Accordingly, it is valuable to the field of pharmaceutical development to identify and characterize previously unknown members of these subfamily of Ras-like proteins. The present invention advances the state of the art by providing a previously unidentified human Ras-like proteins that have homology to members of the RRP22 subfamilies.

Ras Protein

Ras proteins are small regulatory GTP-binding proteins, or small G proteins, which belong to the Ras protein superfamily. They are monomeric GTPases, but their GTPase activity is very slow (less than one GTP molecule per minute).

Ras proteins are key relays in the signal transducing cascade induced by the binding of a ligand to specific receptors such as receptor tyrosine kinases (RTKs), since they trigger the MAP kinase cascade. The ligand can be a growth factor (epidermal growth factor (EGF), platelet-derived growth factor (PDGF) . . . ), insulin, an interleukin (IL), granulocyte colony-stimulating factor (G-CSF), granulocyte/macrophage colony-stimulating factor (GM-CSF) . . . .

Ras proteins contain sequences highly conserved during evolution. Their tertiary structure includes ten loops connecting six strands of beta-sheet and five alpha helices.

In mammalians, there are four Ras proteins, which are encoded by Ha-ras, N-ras, Ki-rasA and Ki-rasB genes. They are composed of about 170 residues and have a relative molecular mass of 21 kD. Ras proteins contain covalently attached modified lipids allowing these proteins to bind to the plasma membrane. Ha-Ras has a C-terminal farnesyl group, a C-terminal palmitoyl group and a N-terminal myristoyl group. In Ki-Ras(B), a C-terminal polylysine domain replaces the palmitoyl group.

Ras proteins alternate between an inactive form bound to GDP and an active form bound to GTP. Their activation results from reactions induced by a guanine nucleotide-exchange factor (GEF). Their inactivation results from reactions catalyzed by a GTPase-activating protein (GAP).

When a Ras protein is activated by a GEF such as a Sos protein, the N-terminal region of a serine/threonine kinase, called "Raf protein", can bind to Ras protein. The C-terminal region of the activated Raf thus formed binds to another protein, MEK, and phosphorylates it on both specific tyrosine and serine residues. Active MEK phosphorylates and activates, in turn, a MAP kinase (ERK1 or ERK2), which is also a serine/threonine kinase. This phosphorylation occurs on both specific tyrosine and threonine residues of MAP kinase.

MAP kinase phosphorylates many different proteins, especially nuclear transcription factors (TFs) which regulate expression of many genes during cell proliferation and differentiation.

Recent researches suggest that, in mammalians, phosphatidyl inositol 3'-kinase (PI3-kinase) might be a target of Ras protein, instead of Raf protein. In certain mutations, the translation of ras genes may produce oncogenic Ras proteins.

Ras-like Protein

Guanine nucleotide-binding proteins (GTP-binding proteins, or G proteins) participate in a wide range of regulatory functions including metabolism, growth, differentiation, signal transduction, cytoskeletal organization, and intracellular vesicle transport and secretion. These proteins control diverse sets of regulatory pathways in response to hormones, growth factors, neuromodulators, or other signaling molecules. When these molecules bind to transmembrane receptors, signals are propagated to effector molecules by intracellular signal transducing proteins. Many of these signal transducing proteins are members of the Ras superfamily.

The Ras superfamily is a class of low molecular weight (LMW) GTP-binding proteins which consist of 21–30 kDa polypeptides. These proteins regulate cell growth, cell cycle control, protein secretion, and intracellular vesicle interaction. In particular, the LMW GTP-binding proteins activate cellular proteins by transducing mitogenic signals involved in various cell functions in response to extracellular signals from receptors (Tavitian, A. (1995) C. R. Seances Soc. Biol. Fil. 189:7–12). During this process, the hydrolysis of GTP acts as an energy source as well as an on-off switch for the GTPase activity of the LMW GTP-binding proteins.

The Ras superfamily is comprised of five subfamilies: Ras, Rho, Ran, Rab, and ADP-ribosylation factor (ARF). Specifically, Ras genes are essential in the control of cell proliferation. Mutations in Ras genes have been associated with cancer. Rho proteins control signal transduction in the process of linking receptors of growth factors to actin polymerization which is necessary for cell division. Rab proteins control the translocation of vesicles to and from membranes for protein localization, protein processing, and secretion. Ran proteins are localized to the cell nucleus and play a key role in nuclear protein import, control of DNA synthesis, and cell-cycle progression. ARF and ARF-like proteins participate in a wide variety of cellular functions including vesicle trafficking, exocrine secretion, regulation of phospholipase activity, and endocytosis.

Despite their sequence variations, all five subfamilies of the Ras superfamily share conserved structural features. Four conserved sequence regions (motifs I–IV) have been studied in the LMW GTP-binding proteins. Motif I is the most variable but has the conserved sequence, GXXXXGK. The lysine residue is essential in interacting with the .beta.- and .gamma.-phosphates of GTP. Motif II, III, and IV contain highly conserved sequences of DTAGQ, NKXD, and EXSAX, respectively. Specifically, Motif II regulates the binding of gamma-phosphate of GTP; Motif III regulates the binding of GTP; and Motif IV regulates the guanine base of GTP. Most of the membrane-bound LMW GTP-binding proteins generally require a carboxy terminal isoprenyl group for membrane association and biological activity. The isoprenyl group is added posttranslationally through recognition of a terminal cysteine residue alone or a terminal cysteine-aliphatic amino acid-aliphatic amino acid-any amino acid (CAAX) motif. Additional membrane-binding energy is often provided by either internal palmitoylation or a carboxy terminal cluster of basic amino acids. The LMW GTP-binding proteins also have a variable effector region, located between motifs I and II, which is characterized as the interaction site for guanine nucleotide exchange factors (GEFs) or GTPase-activating proteins (GAPs). GEFs induce the release of GDP from the active form of the G protein, whereas GAPs interact with the inactive form by stimulating the GTPase activity of the G protein.

The ARF subfamily has at least 15 distinct members encompassing both ARF and ARF-like proteins. ARF proteins identified to date exhibit high structural similarity and ADP-ribosylation enhancing activity. In contrast, several ARF-like proteins lack ADP-ribosylation enhancing activity and bind GTP differently. An example of ARF-like proteins is a rat protein, ARL184. ARL184 has been shown to have a molecular weight of 22 kDa and four functional GTP-binding sites (Icard-Liepkalns, C. et al. (1997) Eur. J. Biochem. 246: 388–393). ARL184 is active in both the cytosol and the Golgi apparatus and is closely associated with acetylcholine release, suggesting that ARL184 is a potential regulatory protein associated with Ca.sup.2+—dependent release of acetylcholine.

A number of Rho GTP-binding proteins have been identified in plasma membrane and cytoplasm. These include RhoA, B and C, and D, rhoG, rac 1 and 2, G25K-A and B, and TC10 (Hall, A. et al. (1993) Philos. Trans. R. Soc. Lond. (Biol.) 340:267–271). All Rho proteins have a CAAX motif which binds a prenyl group and either a palmitoylation site or a basic amino acid-rich region, suggesting their role in membrane-associated functions. In particular, RhoD is a protein which functions in early endosome motility and distribution by inducing rearrangement of actin cytoskeleton and cell surface (Murphy, C. et al. (1996) Nature 384:427–432). During cell adhesion, the Rho proteins are essential for triggering focal complex assembly and integrin-dependent signal transduction (Hotchin, N. A. and Hall, A. (1995) J. Cell Biol. 131:1857–1865).

The Ras subfamily proteins already indicated supra are essential in transducing signals from receptor tyrosine kinases (RTKs) to a series of serine/threonine kinases which control cell growth and differentiation. Mutant Ras proteins, which bind but cannot hydrolyze GTP, are permanently activated and cause continuous cell proliferation or cancer. TC21, a Ras-like protein, is found to be highly expressed in a human teratocarcinoma cell line (Drivas, G. T. et al. (1990) Mol. Cell. Biol. 10:1793–1798). Rin and Rit are characterized as membrane-binding, Ras-like proteins without the lipid-binding CAAX motif and carboxy terminal cysteine (Lee, C. -H. J. et al. (1996) J. Neurosci. 16: 6784–6794). Further, Rin is shown to localize in neurons and have calcium-dependant calmodulin-binding activity.

The discovery of new human Ras-like proteins and the polynucleotides that encode them satisfies a need in the art by providing new compositions which are useful in the diagnosis, prevention, and treatment of inflammation and disorders associated with cell proliferation and apoptosis.

SUMMARY OF THE INVENTION

The present invention is based in part on the identification of amino acid sequences of human Ras-like protein polypeptides and proteins that are related to the RRP22 Ras-like protein subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate Ras-like protein activity in cells and tissues that express the Ras-like protein. Experimental data as provided in FIG. 1 indicates expression in humans in lung small cell carcinomas and in the brain.

DESCRIPTION OF THE FIGURE SHEETS

FIG. 1 provides the nucleotide sequence of a cDNA molecule that encodes the Ras-like protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in lung small cell carcinomas and in the brain.

FIG. 2 provides the predicted amino acid sequence of the Ras-like protein of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the Ras-like protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, the following SNPs were identified: A2455C, A2785G, T3482A, A6189G, T6491C, A7353T, A8688G, G10789C, G11079A, and A12087G.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a Ras-like protein or part of a Ras-like protein and are related to the RRP22 subfamily. Utilizing these sequences, additional genomic sequences were assembled and transcript and/or cDNA sequences were isolated and characterized. Based on this analysis, the present invention provides amino acid sequences of human Ras-like protein polypeptides that are related to the RRP22 subfamily, nucleic acid sequences in the form of transcript sequences, cDNA sequences and/or genomic sequences that encode these Ras-like protein polypeptide, nucleic acid variation (allelic information), tissue distribution of expression, and information about the closest art known protein/peptide/domain that has structural or sequence homology to the Ras-like protein of the present invention.

In addition to being previously unknown, the peptides that are provided in the present invention are selected based on their ability to be used for the development of commercially important products and services. Specifically, the present peptides are selected based on homology and/or structural relatedness to known Ras-like proteins of the RRP22 subfamily and the expression pattern observed. Experimental data as provided in FIG. 1 indicates expression in humans in lung small cell carcinomas and in the brain. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known RRP22 family or subfamily of Ras-like proteins.

Specific Embodiments

Peptide Molecules

The present invention provides nucleic acid sequences that encode protein molecules that have been identified as being members of the Ras-like protein family and are related to the RRP22 subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the Ras-like proteins or peptides of the present invention, Ras-like proteins or peptides, or peptides/proteins of the present invention.

The present invention provides isolated peptide and protein molecules that consist of, consist essentially of, or comprise the amino acid sequences of the Ras-like protein polypeptide disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components.

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the Ras-like protein polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated Ras-like protein polypeptide can be purified from cells that naturally express it, purified from cells that have been altered to express it (recombinant), or synthesized using known protein synthesis methods. Experimental data as provided in FIG. 1 indicates expression in humans in lung small cell carcinomas and in the brain. For example, a nucleic acid molecule encoding the Ras-like protein polypeptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the Ras-like protein polypeptide of the present invention are the naturally occurring mature proteins. A brief description of how various types of these proteins can be made/isolated is provided below.

The Ras-like protein polypeptides of the present invention can be attached to heterologous sequences to form chimeric or fusion proteins. Such chimeric and fusion proteins comprise a Ras-like protein polypeptide operatively linked to a heterologous protein having an amino acid sequence not substantially homologous to the Ras-like protein polypeptide. "Operatively linked" indicates that the Ras-like protein polypeptide and the heterologous protein are fused in-frame. The heterologous protein can be fused to the N-terminus or C-terminus of the Ras-like protein polypeptide.

In some uses, the fusion protein does not affect the activity of the Ras-like protein polypeptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant Ras-like protein polypeptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A Ras-like protein polypeptide-encoding nucleic acid can be cloned into such an expression vector such that the fusion moiety is linked in-frame to the Ras-like protein polypeptide.

As mentioned above, the present invention also provides and enables obvious variants of the amino acid sequence of the peptides of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art know techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the Ras-like protein polypeptides of the present invention. The degree of homology/identity present will be based primarily on whether the peptide is a functional variant or non-functional variant, the amount of divergence present in the paralog family, and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, 40%, 50%, 60%, 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM259 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*CABIOS,* 4:11–17 (1989)) which has been incorporated into the ALIGN program (version 2.0), using a PAM 120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10(1990)). BLAST nucleotide searches can be performed with the NBLAST program, score=100, word length =12 to obtain nucleotide sequences homologous to the nucleic acid molecules of the invention. BLAST protein searches can be performed with the XBLAST program, score=50, word length =3, to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the Ras-like protein polypeptides of the present invention as well as being encoded by the same genetic locus as the Ras-like protein polypeptide provided herein. The gene encoding the novel Ras-like protein of the present invention is located on a genome component that has been mapped to human chromosome 17 (as indicated in FIG. 3), which is supported by multiple lines of evidence, such as STS and BAC map data.

Allelic variants of a Ras-like protein polypeptide can readily be identified as being a human protein having a high degree (significant) of sequence homology/identity to at least a portion of the Ras-like protein polypeptide as well as being encoded by the same genetic locus as the Ras-like protein polypeptide provided herein. Genetic locus can readily be determined based on the genomic information provided in FIG. 3, such as the genomic sequence mapped to the reference human. The gene encoding the novel Ras-like protein of the present invention is located on a genome component that has been mapped to human chromosome 17 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a Ras-like protein polypeptide encoding nucleic acid molecule under stringent conditions as more fully described below.

FIG. 3 provides information on SNPs that have been found in the gene encoding the Ras-like protein of the present invention. The following variations were seen: A2455C, A2785G, T3482A, A6189G, T6491C, A7353T, A8688G, G10789C, GI 1079A, and A12087G. Some of these SNPs, particularly the SNPs 5' of the ORF and in the first intron, may affect control/regulatory elements.

Paralogs of a Ras-like protein polypeptide can readily be identified as having some degree of significant sequence homology/identity to at least a portion of the Ras-like protein polypeptide, as being encoded by a gene from humans, and as having similar activity or function. Two proteins will typically be considered paralogs when the amino acid sequences are typically at least about 40–50%, 50–60%, and more typically at least about 60–70% or more homologous through a given region or domain. Such paralogs will be encoded by a nucleic acid sequence that will hybridize to a Ras-like protein polypeptide encoding nucleic acid molecule under moderate to stringent conditions as more fully described below.

Orthologs of a Ras-like protein polypeptide can readily be identified as having some degree of significant sequence homology/identity to at least a portion of the Ras-like protein polypeptide as well as being encoded by a gene from another organism. Preferred orthologs will be isolated from mammals, preferably primates, for the development of human therapeutic targets and agents. Such orthologs will be encoded by a nucleic acid sequence that will hybridize to a Ras-like protein polypeptide encoding nucleic acid molecule under moderate to stringent conditions, as more fully described below, depending on the degree of relatedness of the two organisms yielding the proteins.

Non-naturally occurring variants of the Ras-like protein polypeptides of the present invention can readily be generated using recombinant techniques. Such variants include, but are not limited to deletions, additions and substitutions in the amino acid sequence of the Ras-like protein polypeptide. For example, one class of substitutions is conserved amino acid substitutions. Such substitutions are those that substitute a given amino acid in a Ras-like protein polypeptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent are found in Bowie et al., Science 247:1306–1310 (1990).

Variant Ras-like protein polypeptides can be fully functional or can lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., Science 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallography, nuclear magnetic resonance, or photoaffinity labeling (Smith et al., J. Mol. Biol. 224:899–904 (1992); de Vos et al. Science 255:306–312 (1992)).

The present invention further provides fragments of the Ras-like protein polypeptides, in addition to proteins and peptides that comprise and consist of such fragments. Particularly those comprising the residues identified in FIG. 2. The fragments to which the invention pertains, however, are not to be construed as encompassing fragments that have been disclosed publicly prior to the present invention.

As used herein, a fragment comprises at least 8, 10, 12, 14, 16 or more contiguous amino acid residues from a Ras-like protein polypeptide. Such fragments can be chosen based on the ability to retain one or more of the biological activities of the Ras-like protein polypeptide, or can be chosen for the ability to perform a function, e.g., act as an immunogen. Particularly important fragments are biologically active fragments, peptides that are, for example about 8 or more amino acids in length. Such fragments will typically comprise a domain or motif of the Ras-like protein polypeptide, e.g., active site. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE, HMMer, eMOTIF, etc.). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in Ras-like protein polypeptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N. Y. Acad. Sci.* 663:48–62 (1992)).

Accordingly, the Ras-like protein polypeptides of the present invention also encompass derivatives or analogs in which a substituted amino acid residue is not one encoded by the genetic code, in which a substituent group is included, in which the mature Ras-like protein polypeptide is fused with another compound, such as a compound to increase the half-life of the Ras-like protein polypeptide (for example, polyethylene glycol), or in which the additional amino acids are fused to the mature Ras-like protein polypeptide, such as a leader or secretory sequence or a sequence for purification of the mature Ras-like protein polypeptide, or a pro-protein sequence.

Protein/Peptide Uses

The proteins of the present invention can be used in assays to determine the biological activity of the protein, including in a panel of multiple proteins for high-throughput screening; to raise antibodies or to elicit another immune response; as a reagent (including the labeled reagent) in assays designed to quantitatively determine levels of the protein (or its ligand or receptor) in biological fluids; and as markers for tissues in which the corresponding protein is preferentially expressed (either constitutively or at a particular stage of tissue differentiation or development or in a disease state). Where the protein binds or potentially binds to another protein (such as, for example, in a receptor-ligand interaction), the protein can be used to identify the binding partner so as to develop a system to identify inhibitors of the binding interaction. Any or all of these research utilities are capable of being developed into reagent grade or kit format for commercialization as research products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, Ras-like proteins isolated from humans and their human/mammalian orthologs serve as targets for identifying agents for use in mammalian therapeutic applications, e.g. a human drug, particularly in modulating a biological or pathological response in a cell or tissue that expresses the Ras-like protein. Experimental data as provided in FIG. 1 indicates that the Ras-like proteins of the present invention are expressed in humans in lung small cell carcinomas (as indicated by virtual northern blot analysis) and in the brain (as indicated by PCR-based tissue screening panels). A large percentage of pharmaceutical agents are being developed that modulate the activity of Ras-like proteins, particularly members of the RRP22 subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in lung small cell carcinomas and in the brain. Such uses can readily be determined using the information provided herein, that which is known in the art, and routine experimentation.

The proteins of the present invention (including variants and fragments that may have been disclosed prior to the present invention) are useful for biological assays related to Ras-like proteins that are related to members of the RRP22 subfamily. Such assays involve any of the known Ras-like protein functions or activities or properties useful for diagnosis and treatment of Ras-like protein-related conditions that are specific for the subfamily of Ras-like proteins that the one of the present invention belongs to, particularly in cells and tissues that express the Ras-like protein. Experimental data as provided in FIG. 1 indicates that the Ras-like proteins of the present invention are expressed in humans in lung small cell carcinomas (as indicated by virtual northern blot analysis) and in the brain (as indicated by PCR-based tissue screening panels).

The proteins of the present invention are also useful in drug screening assays, in cell-based or cell-free systems. Cell-based systems can be native, i.e., cells that normally express the Ras-like protein, as a biopsy or expanded in cell culture. Experimental data as provided in FIG. 1 indicates expression in humans in lung small cell carcinomas and in the brain. In an alternate embodiment, cell-based assays involve recombinant host cells expressing the Ras-like protein.

The polypeptides can be used to identify compounds that modulate Ras-like protein activity. Both the Ras-like protein of the present invention and appropriate variants and fragments can be used in high-throughput screens to assay candidate compounds for the ability to bind to the Ras-like protein. These compounds can be further screened against a functional Ras-like protein to determine the effect of the compound on the Ras-like protein activity. Further, these compounds can be tested in animal or invertebrate systems to determine activity/effectiveness. Compounds can be identified that activate (agonist) or inactivate (antagonist) the Ras-like protein to a desired degree.

Therefore, in one embodiment, RRP22 or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, a pharmaceutical composition comprising RRP22 may be administered to a subject to prevent or treat a disorder associated with increased apoptosis including, but not limited to, those listed above.

In still another embodiment, an agonist which is specific for RRP22 may be administered to prevent or treat a disorder associated with increased apoptosis including, but not limited to, those listed above.

In a further embodiment, a vector capable of expressing RRP22, or a fragment or a derivative thereof, may be used to prevent or treat a disorder associated with increased apoptosis including, but not limited to, those listed above.

In cancer, where RRP22 promotes cell proliferation, it is desirable to decrease its activity. Therefore, in one embodiment, an antagonist of RRP22 may be administered to a subject to prevent or treat cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for RRP22 may be used directly as an antagonist, or indirectly as a targeting or delivery mechanism for bringing a pharmaceutical agent to cells or tissue which express RRP22.

In another embodiment, a vector expressing the complement of the polynucleotide encoding RRP22 may be administered to a subject to prevent or treat a cancer including, but not limited to, the types of cancer listed above.

In inflammation, where RRP22 promotes cell proliferation, it is desirable to decrease its activity. Therefore, in one embodiment, an antagonist of RRP22 may be administered to a subject to prevent or treat an inflammation. Disorders associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for RRP22 may be used directly as an antagonist, or indirectly as a targeting or delivery mechanism for bringing a pharmaceutical agent to cells or tissue which express RRP22.

Further, the Ras-like protein polypeptides can be used to screen a compound for the ability to stimulate or inhibit interaction between the Ras-like protein and a molecule that normally interacts with the Ras-like protein, e.g. a ligand or a component of the signal pathway that the Ras-like protein normally interacts. Such assays typically include the steps of combining the Ras-like protein with a candidate compound under conditions that allow the Ras-like protein, or fragment, to interact with the target molecule, and to detect the formation of a complex between the protein and the target or to detect the biochemical consequence of the interaction with the Ras-like protein and the target, such as any of the associated effects of signal transduction.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries). (Hodgson, Bio/technology, 1992, Sept 10(9);973–80).

One candidate compound is a soluble fragment of the Ras-like protein that competes for ligand binding. Other candidate compounds include mutant Ras-like proteins or appropriate fragments containing mutations that affect Ras-like protein function and thus compete for ligand. Accordingly, a fragment that competes for ligand, for example with a higher affinity, or a fragment that binds ligand but does not allow release, is within the scope of the invention.

The invention further includes other end point assays to identify compounds that modulate (stimulate or inhibit) Ras-like protein activity. The assays typically involve an assay of events in the Ras-like protein mediated signal transduction pathway that indicate Ras-like protein activity. Thus, the phosphorylation of a protein/ligand target, the expression of genes that are up- or down-regulated in response to the Ras-like protein dependent signal cascade can be assayed. In one embodiment, the regulatory region of such genes can be operably linked to a marker that is easily detectable, such as luciferase. Alternatively, phosphorylation of the Ras-like protein, or a Ras-like protein target, could also be measured.

Any of the biological or biochemical functions mediated by the Ras-like protein can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric Ras-like proteins in which any of the protein's domains, or parts thereof, can be replaced by heterologous domains or subregions. Accordingly, a different set of signal transduction components is available as an end-point assay for activation. This allows for assays to be performed in other than the specific host cell from which the Ras-like protein is derived.

The Ras-like protein polypeptide of the present invention is also useful in competition binding assays in methods designed to discover compounds that interact with the Ras-like protein. Thus, a compound is exposed to a Ras-like protein polypeptide under conditions that allow the compound to bind or to otherwise interact with the polypeptide. Soluble Ras-like protein polypeptide is also added to the mixture. If the test compound interacts with the soluble Ras-like protein polypeptide, it decreases the amount of complex formed or activity from the Ras-like protein target. This type of assay is particularly useful in cases in which compounds are sought that interact with specific regions of the Ras-like protein. Thus, the soluble polypeptide that competes with the target Ras-like protein region is designed to contain peptide sequences corresponding to the region of interest.

To perform cell free drug screening assays, it is sometimes desirable to immobilize either the Ras-like protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/15625 fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of Ras-like protein-binding protein found in the bead fraction quantitated from the gel using standard electrophoretic techniques. For example, either the polypeptide or its target molecule can be immobilized utilizing conjugation of biotin and streptavidin with techniques well known in the art. Alternatively, antibodies reactive with the protein but which do not interfere with binding of the protein to its target molecule can be derivatized to the wells of the plate, and the protein trapped in the wells by antibody conjugation. Preparations of a Ras-like protein-binding protein and a candidate compound are incubated in the Ras-like protein-presenting wells and the amount of complex trapped in the well can be quantitated. Methods for detecting such complexes, in addition to those described above for the GST-immobilized complexes, include immunodetection of complexes using antibodies reactive with the Ras-like protein target molecule, or which are reactive with Ras-like protein and compete with the target molecule, as well as enzyme-linked assays which rely on detecting an enzymatic activity associated with the target molecule.

Agents that modulate one of the Ras-like proteins of the present invention can be identified using one or more of the above assays, alone or in combination. It is generally preferable to use a cell-based or cell free system first and then confirm activity in an animal/insect model system. Such model systems are well known in the art and can readily be employed in this context.

Modulators of Ras-like protein activity identified according to these drug screening assays can be used to treat a subject with a disorder mediated by the Ras-like protein associated pathway, by treating cells that express the Ras-like protein. Experimental data as provided in FIG. 1 indicates expression in humans in lung small cell carcinomas and in the brain. These methods of treatment include the steps of administering the modulators of protein activity in a pharmaceutical composition as described herein, to a subject in need of such treatment.

In yet another aspect of the invention, the Ras-like proteins can be used as "bait proteins" in a two-hybrid assay or three-hybrid assay (see, e.g., U.S. Pat. No. 5,283,317; Zervos et al., *Cell* 72:223–232 (1993); Madura et al., *J. Biol. Chem.* 268:12046–12054 (1993); Bartel et al., *Biotechniques* 14:920–924 (1993); Iwabuchi et al., *Oncogene* 8:1693–1696 (1993); and Brent WO94/10300), to identify other proteins that bind to or interact with the Ras-like protein and are involved in Ras-like protein activity. Such Ras-like protein-binding proteins are also likely to be involved in the propagation of signals by the Ras-like proteins or Ras-like protein targets as, for example, downstream elements of a Ras-like protein-mediated signaling pathway, e.g., a pain signaling pathway. Alternatively, such Ras-like protein-binding proteins are likely to be Ras-like protein inhibitors.

The two-hybrid system is based on the modular nature of most transcription factors, which consist of separable DNA-binding and activation domains. Briefly, the assay utilizes two different DNA constructs. In one construct, the gene that codes for a Ras-like protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a Ras-like protein-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the Ras-like protein.

This invention further pertains to novel agents identified by the above-described screening assays. Accordingly, it is within the scope of this invention to further use an agent identified as described herein in an appropriate animal model. For example, an agent identified as described herein (e.g., a Ras-like protein modulating agent, an antisense Ras-like protein nucleic acid molecule, a Ras-like protein-specific antibody, or a Ras-like protein-binding partner) can be used in an animal or insect model to determine the efficacy, toxicity, or side effects of treatment with such an agent. Alternatively, an agent identified as described herein can be used in an animal or insect model to determine the mechanism of action of such an agent. Furthermore, this invention pertains to uses of novel agents identified by the above-described screening assays for treatments as described herein.

The Ras-like proteins of the present invention are also useful to provide a target for diagnosing a disease or predisposition to a disease mediated by the peptide, Accordingly, the invention provides methods for detecting the presence, or levels of, the protein (or encoding mRNA) in a cell, tissue, or organism. Experimental data as provided in FIG. 1 indicates expression in humans in lung small cell carcinomas and in the brain. The method involves contacting a biological sample with a compound capable of interacting with the receptor protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells, and fluids present within a subject.

The peptides also are useful to provide a target for diagnosing a disease or predisposition to a disease mediated by the peptide, Accordingly, the invention provides methods for detecting the presence, or levels of, the protein in a cell, tissue, or organism. The method involves contacting a biological sample with a compound capable of interacting with the receptor protein such that the interaction can be detected.

The peptides of the present invention also provide targets for diagnosing active disease, or predisposition to a disease, in a patient having a variant peptide. Thus, the peptide can be isolated from a biological sample and assayed for the presence of a genetic mutation that results in translation of an aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered receptor activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations, and immunofluorescence using a detection reagents, such as an antibody or protein binding agent. Alternatively, the peptide can be detected in vivo in a subject by introducing into the subject a labeled anti-peptide antibody. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the receptor protein in which one or more of the receptor functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and receptor activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in lung small cell carcinomas and in the brain. Accordingly, methods for treatment include the use of the Ras-like protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the FIGS.

Antibodies are preferably prepared from regions or discrete fragments of the Ras-like proteins. Antibodies can be prepared from any region of the peptide as described herein. However, preferred regions will include those involved in function/activity and/or receptor/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection of an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the Ras-like proteins of the present invention are expressed in humans in lung small cell carcinomas (as indicated by virtual northern blot analysis) and in the brain (as indicated by PCR-based tissue screening panels). Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development. Antibody detection of circulating fragments of the full-length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in lung small cell carcinomas and in the brain. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in lung small cell carcinomas and in the brain. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in lung small cell carcinomas and in the brain. Thus, where a specific protein has been correlated with expression in a specific tissue, antibodies that are specific for this protein can be used to identify a tissue type.

The antibodies are also useful for inhibiting protein function, for example, blocking the binding of the Ras-like protein to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use.

Nucleic Acid Molecules

The present invention further provides isolated nucleic acid molecules that encode a Ras-like protein polypeptide of the present invention. Such nucleic acid molecules will consist of, consist essentially of, or comprise a nucleotide sequence that encodes one of the Ras-like protein polypeptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule. The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the FIGURES will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

Full-length genes may be cloned from known sequence using any one of a number of methods known in the art. For example, a method which employs XL-PCR (Perkin-Elmer, Foster City, Calif.) to amplify long pieces of DNA may be used. Other methods for obtaining full-length sequences are well known in the art.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life, or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the Ras-like protein polypeptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, MRNA processing (including splicing and polyadenylation signals), ribosome binding, and stability of mRNA. In addition, the nucleic acid molecule may be fused to a marker sequence encoding, for example, a peptide that facilitates purification.

Isolated nucleic acid molecules can be in the form of RNA, such as mRNA, or in the form of DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention and that encode obvious variants of the Ras-like proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or whole organisms. Accordingly, as discussed above, the variants can contain nucleotide substitutions, deletions inversions, and/or insertions. Variation can occur in either or both the coding and non-coding regions. The variations can produce both conservative and non-conservative amino acid substitutions.

The present invention further provides non-coding fragments of the nucleic acid molecules provided in the FIGS. 1 and 3. Preferred non-coding fragments include, but are not limited to, promoter sequences, enhancer sequences, gene modulating sequences, and gene termination sequences. Such fragments are useful in controlling heterologous gene expression and in developing screens to identify gene-modulating agents.

A fragment comprises a contiguous nucleotide sequence greater than 12 or more nucleotides. Further, a fragment could be at least 30, 40, 50, 100 250, or 500 nucleotides in length. The length of the fragment will be based on its intended use. For example, the fragment can encode epitope-bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50, or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the FIG. sheets or a fragment of this sequence. Such nucleic acid molecules can readily be identified as being able to hybridize under moderate to stringent conditions, to the nucleotide sequence shown in the FIG. sheets or a fragment of the sequence. The gene encoding the novel Ras-like protein of the present invention is located on a genome component that has been mapped to human chromosome 17 (as indicated in FIG. 3), which is supported by multiple lines of evidence, such as STS and BAC map data.

FIG. 3 provides information on SNPs that have been found in the gene encoding the Ras-like protein of the present invention. The following variations were seen: A2455C, A2785G, T3482A, A6189G, T6491C, A7353T, A8688G, G10789C, GI 1079A, and A12087G. Some of these SNPs, particularly the SNPs 5' of the ORF and in the first intron, may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6X sodium chloride/sodium citrate (SSC) at about 45C, followed by one or more washes in 0.2 X SSC, 0.1% SDS at 50–65° C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, the following SNPs were identified: A2455C, A2785G, T3482A, A6189G, T6491C, A7353T, A8688G, G10789C, G11079A, and A12087G.

The probe can correspond to any sequence along the entire length of the nucleic acid molecules provided in the FIGS. Accordingly, it could be derived from 5' noncoding regions, the coding region, and 3' noncoding regions. However, as discussed, fragments are not to be construed as those, which may encompass fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel Ras-like protein of the present invention is located on a genome component that has been mapped to human chromosome 17 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for constructing host cells expressing a part, or all, of the nucleic acid molecules and peptides. Moreover, the nucleic acid molecules are useful for constructing transgenic animals wherein a homolog of the nucleic acid molecule has been "knocked-out" of the animal's genome.

The nucleic acid molecules are also useful for constructing transgenic animals expressing all, or a part, of the nucleic acid molecules and peptides.

The nucleic acid molecules are also useful for making vectors that express part, or all, of the peptides.

The nucleic acid molecules are also useful as hybridization probes for determining the presence, level, form, and distribution of nucleic acid expression. Experimental data as provided in FIG. 1 indicates that the Ras-like proteins of the present invention are expressed in humans in lung small cell carcinomas (as indicated by virtual northern blot analysis) and in the brain (as indicated by PCR-based tissue screening panels). Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in Ras-like protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a Ras-like protein, such as by measuring a level of a receptor-encoding nucleic acid in a sample of cells from a subject e.g., mRNA or genomic DNA, or determining if a receptor gene has been mutated. Experimental data as provided in FIG. 1 indicates that the Ras-like proteins of the present invention are expressed in humans in lung small cell carcinomas (as indicated by virtual northern blot analysis) and in the brain (as indicated by PCR-based tissue screening panels).

Nucleic acid expression assays are useful for drug screening to identify compounds that modulate Ras-like protein nucleic acid expression.

The invention thus provides a method for identifying a compound that can be used to treat a disorder associated with nucleic acid expression of the Ras-like protein gene, particularly biological and pathological processes that are mediated by the Ras-like protein in cells and tissues that express it. Experimental data as provided in FIG. 1 indicates expression in humans in lung small cell carcinomas and in the brain. The method typically includes assaying the ability of the compound to modulate the expression of the Ras-like protein nucleic acid and thus identifying a compound that can be used to treat a disorder characterized by undesired Ras-like protein nucleic acid expression. The assays can be performed in cell-based and cell-free systems. Cell-based assays include cells naturally expressing the Ras-like protein nucleic acid or recombinant cells genetically engineered to express specific nucleic acid sequences.

The assay for Ras-like protein nucleic acid expression can involve direct assay of nucleic acid levels, such as MRNA levels, or on collateral compounds involved in the signal pathway. Further, the expression of genes that are up- or down-regulated in response to the Ras-like protein signal pathway can also be assayed. In this embodiment the regulatory regions of these genes can be operably linked to a reporter gene such as luciferase.

Thus, modulators of Ras-like protein gene expression can be identified in a method wherein a cell is contacted with a candidate compound and the expression of mRNA determined. The level of expression of Ras-like protein mRNA in the presence of the candidate compound is compared to the level of expression of Ras-like protein MRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate Ras-like protein nucleic acid expression in cells and tissues that express the Ras-like protein. Experimental data as provided in FIG. 1 indicates that the Ras-like proteins of the present invention are expressed in humans in lung small cell carcinomas (as indicated by virtual northern blot analysis) and in the brain (as indicated by PCR-based tissue screening panels). Modulation includes both up-regulation (i.e. activation or agonization) or down-regulation (suppression or antagonization) of nucleic acid expression.

Alternatively, a modulator for Ras-like protein nucleic acid expression can be a small molecule or drug identified using the screening assays described herein as long as the drug or small molecule inhibits the Ras-like protein nucleic acid expression in the cells and tissues that express the protein. Experimental data as provided in FIG. 1 indicates expression in humans in lung small cell carcinomas and in the brain.

The nucleic acid molecules are also useful for monitoring the effectiveness of modulating compounds on the expression or activity of the Ras-like protein gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in Ras-like protein nucleic acid, and particularly in qualitative changes that lead to pathology. The nucleic acid molecules can be used to detect mutations in Ras-like protein genes and gene expression products such as mRNA. The nucleic acid molecules can be used as hybridization probes to detect naturally occurring genetic mutations in the Ras-like protein gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns, or changes in gene copy number, such as amplification. Detection of a mutated form of the Ras-like protein gene associated with a dysfunction provides a diagnostic tool for an active disease or susceptibility to disease when the disease results from overexpression, underexpression, or altered expression of a Ras-like protein.

Individuals carrying mutations in the Ras-like protein gene can be detected at the nucleic acid level by a variety of techniques. FIG. 3 provides information on SNPs that have been found in the gene encoding the Ras-like protein of the present invention. The following variations were seen: A2455C, A2785G, T3482A, A6189G, T6491C, A7353T, A8688G, G10789C, GI 1079A, and A12087G. Some of these SNPs, particularly the SNPs 5' of the ORF and in the first intron, may affect control/regulatory elements. The gene encoding the novel Ras-like protein of the present invention is located on a genome component that has been mapped to human chromosome 17 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a Ras-like protein gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant Ras-like protein gene and a wild-type gene can be determined by direct DNA sequencing. A variety of automated sequencing procedures can be utilized when performing the diagnostic assays (Naeve, C. W., *Biotechniques* 19:448 (1995)), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include, selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the Ras-like protein gene in an individual in order to select an appropriate compound or dosage regimen for treatment. FIG. 3 provides information on SNPs that have been found in the gene encoding the Ras-like protein of the present invention. The following variations were seen: A2455C, A2785G, T3482A, A6189G, T6491 C, A7353T, A8688G, G10789C, G11079A, and A12087G. Some of these SNPs, particularly the SNPs 5' of the ORF and in the first intron, may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control Ras-like protein gene expression in cells, tissues, and organisms. A DNA antisense nucleic acid molecule is designed to be complementary to a region of the gene involved in transcription, preventing transcription and hence production of Ras-like protein. An antisense RNA or DNA nucleic acid molecule would hybridize to the MRNA and thus block translation of mRNA into Ras-like protein.

Alternatively, a class of antisense molecules can be used to inactivate MRNA in order to decrease expression of Ras-like protein nucleic acid. Accordingly, these molecules can treat a disorder characterized by abnormal or undesired Ras-like protein nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the Ras-like protein, such as ligand binding.

The nucleic acid molecules also provide vectors for gene therapy in patients containing cells that are aberrant in Ras-like protein gene expression. Thus, recombinant cells, which include the patient's cells that have been engineered ex vivo and returned to the patient, are introduced into an individual where the cells produce the desired Ras-like protein to treat the individual.

The invention also encompasses kits for detecting the presence of a Ras-like protein nucleic acid in a biological sample. Experimental data as provided in FIG. 1 indicates that the Ras-like proteins of the present invention are expressed in humans in lung small cell carcinomas (as indicated by virtual northern blot analysis) and in the brain (as indicated by PCR-based tissue screening panels). For example, the kit can comprise reagents such as a labeled or labelable nucleic acid or agent capable of detecting Ras-like protein nucleic acid in a biological sample; means for determining the amount of Ras-like protein nucleic acid in the sample; and means for comparing the amount of Ras-like protein nucleic acid in the sample with a standard. The compound or agent can be packaged in a suitable container. The kit can further comprise instructions for using the kit to detect Ras-like protein mRNA or DNA.

Nucleic Acid Arrays

The present invention further provides arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application W095/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et. al., U.S. Pat. No. 5,807,522.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides that are only 7–20 nucleotides in length. The microarray may contain oligonucleotides that cover the known 5', or 3', sequence, sequential oligonucleotides that cover the full-length sequence; or unique oligonucleotides selected from particular areas along the length of the sequence. Polynucleotides used in the microarray may be oligonucleotides that are specific to a gene or genes of interest.

In order to produce oligonucleotides to a known sequence for a microarray, the gene(s) of interest (or an ORF identified from the contigs of the present invention) is typically examined using a computer algorithm that starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/25 1116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of one or more of the proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention. FIG. 3 provides information on SNPs that have been found in the gene encoding the Ras-like protein of the present invention. The following variations were seen: A2455C, A2785G, T3482A, A6189G, T6491C, A7353T, A8688G, G10789C, G1 1079A, and A12087G. Some of these SNPs, particularly the SNPs 5' of the ORF and in the first intron, may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the human genome disclosed herein; and (b) one or more other containers comprising one or more of the following: wash reagents, reagents capable of detecting presence of a bound nucleic acid. Preferred kits will include chips that are capable of detecting the expression of 10 or more, 100 or more, or 500 or more, 1000 or more, or all of the genes expressed in Human.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified Ras-like protein genes of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning. A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces,* and *Salmonella typhimurium.* Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroRas-like protein. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET11d (Studier et al., *Gene Expression Technology. Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology. Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufinan etal., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance, propagation, or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed, Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced, or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a Ras-like protein polypeptide that can be further purified to produce desired amounts of Ras-like protein or fragments. Thus, host cells containing expression vectors are useful for peptide production.

Host cells are also useful for conducting cell-based assays involving the Ras-like protein or Ras-like protein fragments. Thus, a recombinant host cell expressing a native Ras-like protein is useful for assaying compounds that stimulate or inhibit Ras-like protein function.

Host cells are also useful for identifying Ras-like protein mutants in which these functions are affected. If the mutants naturally occur and give rise to a pathology, host cells containing the mutations are useful to assay compounds that have a desired effect on the mutant Ras-like protein (for example, stimulating or inhibiting function) which may not be indicated by their effect on the native Ras-like protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a Ras-like protein and identifying and evaluating modulators of Ras-like protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the Ras-like protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the Ras-like protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic MRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, Ras-like protein activation, and signal transduction, may not be evident from in vitro cell-free or cell-based assays. Accordingly, it is useful to provide non-human transgenic animals to assay in vivo Ras-like protein function, including ligand interaction, the effect of specific mutant Ras-like proteins on Ras-like protein function and ligand interaction, and the effect of chimeric Ras-like proteins. It is also possible to assess the effect of null mutations, which is mutations that substantially or completely eliminate one or more Ras-like protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

That which is claimed is:

1. An isolated nucleic acid molecule consisting of a nucleotide sequence selected from the group consisting of:
   (a) a nucleotide sequence that encodes a polypeptide comprising the amino acid sequence of SEQ ID NO:2;
   (b) a nucleotide sequence consisting of SEQ ID NO:1;
   (c) a nucleotide sequence consisting of SEQ ID NO:3; and
   (d) a nucleotide sequence that is completely complementary over the entire length of a nucleotide sequence of (a)–(c).

2. A vector comprising the nucleic acid molecule of claim 1.

3. The vector of claim 2, wherein said vector is selected from the group consisting of a plasmid, a virus, and a bacteriophage.

4. The vector of claim 2, wherein said isolated nucleic acid molecule is inserted into said vector in proper orientation and correct reading frame such that a polypeptide comprising SEQ ID NO:2 may be expressed by a cell transformed with said vector.

5. The vector of claim 4, wherein said isolated nucleic acid molecule is operatively linked to a promoter sequence.

6. An isolated host cell containing the vector of claim 2.

7. A process for producing a polypeptide comprising the amino acid sequence of SEQ ID NO:2, the process comprising culturing the host cell of claim 6 under conditions sufficient for the production of said polypeptide, and recovering said polypeptide, thereby producing said polypeptide.

8. An isolated polynucleotide consisting of the nucleotide sequence of SEQ ID NO:1.

9. An isolated polynucleotide consisting of the nucleotide sequence of SEQ ID NO:3.

* * * * *

SEQUENCE LISTING

<160> NUMBER OF SEQ ID NOS: 20

<210> SEQ ID NO 1
<211> LENGTH: 3192
<212> TYPE: DNA
<213> ORGANISM: Human

<400> SEQUENCE: 1
cctcggcggc ccgcatctgc ccccgcgcgc ccgccctgag cccgccccga ctgggcaggc    60

-continued

```
gggggagccc ctacttctct cccccccgggc gggggagccg gggggcagcg ccggagcccg      120 ggggagctc agccccgccg accggccggc cagggcaggg ggcagctagg acggccccgg        180
tccaggtgga ggccgcagag ggcccagggc aagcagaggc agcaatggtt ggtcctgacg       240
gtggctgagc ccccagcccc tggaatatgc agcccggggg agcccagac agcggcaagg       300 acgaggtggc ggagtggggc gggaggcatg gtctccacct accgggtggc cgtgctgggg      360
gcgcgaggtg tgggcaagag tgccatcgtg cgccagttct tgtacaacga gttcagcgag      420
gtctgcgtcc ccaccaccgc ccgccgcctt tacctgcctg ctgtcgtcat gaacggccac      480
gtgcacgacc tccagatcct cgactttcca cccatcagcg ccttccctgt caatacgctc      540
caggagtggg cagacacctg ctgcagggga ctccggagtg tccacgccta catcctggtc      600
tacgacatct gctgctttga cagctttgag tacgtcaaga ccatccgcca gcagatcctg      660
gagacgaggg tgatcggaac ctcagagacg cccatcatca tcgtgggcaa caagcgggac      720
ctgcagcgcg gacgcgtgat cccgcgctgg aacgtgtcgc acctggtacg caagacctgg      780
aagtgcggct acgtggaatg ctcggccaag tacaactggc acatcctgct gctcttcagc      840
gagctgctca agagcgtcgg ctgcgcccgt tgcaagcacg tgcacgctgc cctgcgcttc      900
cagggcgcgc tgccgcaa ccgctgcgcc atcatgtgac gcctgcgcgc ccctcgggct       960
gcaccggcac tggccgagcg gagggcgggg ccgtactgcg gggctggggc ggggagcggg     1020
cgggaaatgg aactgtgacg gtcccggcct gaggcccctg cagccacgca cctcccggtg     1080
agaagcagag cgcgagaggg agccctccgt aactgcccag ccctgcccct tgccccgtg     1140 gcttcctggg acagccgcct tcagtgctgt atttagtgca gtgcccggcc cgaccgcgg     1200 gggtgccaca gccttttggg atgggggtga gcgtgcaatg gaggctgggg gtggcgaggt     1260
gccgccttgg ccgggccccc acgtgtcttc tccagaatgt gtctgtcttt gcctggtgtc     1320
ttcctttccc gtgtccgccc accccagcgt ctgttggtac ttacctgtct cacctaccct    1380
ccagtcccct cccagctccg ctcacagggc tctcatttcg tccatcccct tgtcgcagat    1440
cctggcagct tctttgtgag gccaggcctt ctgactgtca gcaccaccgg cacagggcag    1500
agatgcgggt ggcccaagga ccacgatcaa ggggtccggg ggaccgaggt cccagatcag    1560
tgagggagga aggttgagct ctccggcttc agggagacc tccccgccca gcagccccca    1620
gagacacaac aacctacctt ccagccttaa ctcgatggtc cgtccctgcc aggtgcccct    1680
cactcttcct gaccccaaag ccagatcacc ccctggggtta aaactttttt tcttttttt    1740 ttttggacag agtgtggaaa gggagccccc caaaggatag cttcttttc atgatgccag     1800 gctccagtcc tttattccct tctgcatact gcaatctgat ctgtcagact ggggaatgtt    1860
gggtctgggg gtctggtcgt gggcaggatg gtgcccagaa gggggttagg ttgtcccagt     1920
gaaaattctg ttgcccccgtc tcaacccat ctgactaccc cagactctgc ctgcctcaga    1980
tctcagacta tcctgattaa tctggggaag aacagagcca gggaaagaat ggtggggacc    2040
cctgtacttg ggggagacac acctgcatct tcctcctgcc acagatggag gccctcagga    2100
tctgacaccc tcttgtccca acaccagtca gccctatacc ctaactcact ccaccccatt    2160
ttctccggct gcctggccgg gtttctacct ctcgtcaccg gagctgatca ctgtcagttt    2220
tgtaccgatt tagaaataac aataataatg aagattctag gaatggcatg agggattgat    2280
gggggacttg gagggaggga caagtggtgc cctgtcccct gctcccctgg ccaaagaaag    2340
ctgtccttga ggctgagccc tcagccctgg cctggtgggg ggacagcaag gtcccttgtt    2400
```

-continued

| | |
|---|---|
| ataagagggg cagagaggac aactccgctt tggccaacct agccaaggct gcagcatata | 2460 |
| gaccaggaaa tcaggtagcc cagactggtg atggagcaga gtctggggga agggtcgtgg | 2520 |
| gtggggaatt tatcaccaac atccattgta gggggaatct atgattctgc ttccccagcg | 2580 |
| gattcccact ctgtccacca agtgggggt agcacagcct cacagcaacc gccctgacct | 2640 |
| tgggcagtct agtgttcctg cattctagtc cctgctgtgc tgcaggactt tgggcaagtg | 2700 |
| acctgccctc tgtgagcctc cctctgacac agaggaggtg gctccccttc cccacacctt | 2760 |
| agagtggctg ggagggtaac aaagagggcc tgccccttta gtctcctgca ccctgcccc | 2820 |
| ctggttcacc agagggagcg gatgaaggat ggcagcatct cacatgcccc atcaccaact | 2880 |
| ctgaggcacc tggggtgggg gggcggagcc caggcctctg gctgctcccc tgtgggagcc | 2940 |
| attggaatgt atcccctgac aggccccctt ccgcctccac ctcaacccag gtcttggatt | 3000 |
| tcaggtccct ccaccccat tctgagtctc tgtccttctc cttccacccg ctcccagggt | 3060 |
| ttcccaccac agggtctgga agtgtgtgtg acgcccattg agctgttacc cgaagtcaga | 3120 |
| ttaaaaatca gggagtgttt tccctcgttt ctgtaaaaaa aaaaaaaaaa aaaaaaaaaa | 3180 |
| aaaaaaaaaa aa | 3192 |

<210> SEQ ID NO 2
<211> LENGTH: 203
<212> TYPE: PRT
<213> ORGANISM: Human

<400> SEQUENCE: 2

Met Val Ser Thr Tyr Arg Val Ala Val Leu Gly Ala Arg Gly Val Gly
1               5                   10                  15

Lys Ser Ala Ile Val Arg Gln Phe Leu Tyr Asn Glu Phe Ser Glu Val
            20                  25                  30

Cys Val Pro Thr Thr Ala Arg Arg Leu Tyr Leu Pro Ala Val Val Met
        35                  40                  45

Asn Gly His Val His Asp Leu Gln Ile Leu Asp Phe Pro Pro Ile Ser
    50                  55                  60

Ala Phe Pro Val Asn Thr Leu Gln Glu Trp Ala Asp Thr Cys Cys Arg
65                  70                  75                  80

Gly Leu Arg Ser Val His Ala Tyr Ile Leu Val Tyr Asp Ile Cys Cys
                85                  90                  95

Phe Asp Ser Phe Glu Tyr Val Lys Thr Ile Arg Gln Gln Ile Leu Glu
            100                 105                 110

Thr Arg Val Ile Gly Thr Ser Glu Thr Pro Ile Ile Val Gly Asn
        115                 120                 125

Lys Arg Asp Leu Gln Arg Gly Arg Val Ile Pro Arg Trp Asn Val Ser
    130                 135                 140

His Leu Val Arg Lys Thr Trp Lys Cys Gly Tyr Val Glu Cys Ser Ala
145                 150                 155                 160

Lys Tyr Asn Trp His Ile Leu Leu Phe Ser Glu Leu Leu Lys Ser
                165                 170                 175

Val Gly Cys Ala Arg Cys Lys His Val His Ala Ala Leu Arg Phe Gln
            180                 185                 190

Gly Ala Leu Arg Arg Asn Arg Cys Ala Ile Met
        195                 200

<210> SEQ ID NO 3
<211> LENGTH: 12118
<212> TYPE: DNA

<213> ORGANISM: Human

<400> SEQUENCE: 3

| | | | | | |
|---|---|---|---|---|---|
| ggcgaacgtg | gttggaacaa | acagctggca | gacttgtgac | ccggccctcg | ggatccgcga | 60 |
| agcccccgct | ctcagccttg | ggcagcgacc | caggtgtcca | gacgcaggga | agggacgga | 120 |
| accaggcttc | gccccctgtg | tgtgtctctg | gtctcttgcc | tctctttccg | ggcagtctct | 180 |
| tgccgggcgc | tgtctgcaga | ctcactgcag | agcgcaggcc | ttggggagaa | agcgctcagg | 240 |
| ggcctgggcc | ctgcttcctg | gacagcccc | ctcccttccg | cactcagcca | agggtgttgg | 300 |
| attaatatac | tcttagatcc | aggacctctg | cctggaaaga | aggaaggggc | accgatcgct | 360 |
| tctgagttgg | ggacagggcc | acacttggac | ctgatgagtt | ccaggaggct | ggccccagcc | 420 |
| tagggcctc | ctgcaccccc | ttcctagctc | ctgggtagtg | cccctcttgc | atttccctgc | 480 |
| cgctccccag | aaagggctgg | tttctgggca | gggagtgtgg | tgtccgcgac | aatctgcagg | 540 |
| tagggtgcat | cctagaaatc | tctgagctgc | cacacccaga | gagaggccag | gactcttctt | 600 |
| ggcgttcctt | gccctctctt | cctccccag | gactccccac | tccccacctg | cctgtactgg | 660 |
| ttatgtaatt | aacccagctg | agtctctctg | ccatgctggt | ggtagtggtg | tccagggatg | 720 |
| cctaaggggc | ttcgggacct | ggagggacac | atggggagga | gggataggta | cttccccta | 780 |
| gttgggagcc | catgtaagtg | tataaacacc | tgttggagaa | gggacactgc | atggggcagg | 840 |
| aaggagttca | gggtcctaat | cttagttaac | aactcaactg | gctatgaggt | cttcacttcc | 900 |
| ctaagtcact | gggtttgttt | tttggggggt | ttgtttgttt | tttaaacctt | caataaaatg | 960 |
| agaagaatct | ctctcacgca | cactgcatgc | atgtgagctc | atgcaacagt | agatagcagc | 1020 |
| ccctcctggg | attgctagga | ggttccactg | ctaagtttgt | gggaagctta | gatgaatgaa | 1080 |
| tgaccctgc | ccatagcagt | ggtcactgtt | tattgaacac | ctactctggc | ctaggcactg | 1140 |
| ggctttacat | gcacacatca | taacacttaa | taaagttct | tgcccaaggt | cacacttcag | 1200 |
| gtgaatggca | gagctaggaa | tcaagccctg | gcggttctca | ttccacatcc | tgacctgtat | 1260 |
| ttactatgct | gtgtgcgcac | ataccccgtg | gagtgagtcc | tctgaaccag | acaacctgg | 1320 |
| gggacattca | gctgtggctt | gtgcatatgt | ggaaagaaca | tgcatctgca | gagaagtatg | 1380 |
| cacccatgcg | gaaaagcatg | gccttgccag | aatccggcga | acccacctgc | cctggagcca | 1440 |
| gttagcaagt | gctgatgtca | ccctcctggg | aatccagaca | ggaggtctca | ggcatgtaac | 1500 |
| agcctctctg | gtcaccatca | ccaacaaaag | aagaaaggtt | ctctcctttt | cctggctaag | 1560 |
| agatttactt | ggattttctc | agaagtaggg | gctgttgacc | tcattttacc | tatgtgcaga | 1620 |
| agcatggctc | cagttgagaa | ggtgatttgc | ccactgacct | gcagcaagga | cacaccagag | 1680 |
| ctgatgaatt | cgtatcaagg | cccaaacccc | tagcagccct | tttctgggca | cctgctatgt | 1740 |
| gccaggcccct | ctgggctcta | ggggatgcca | gagaatcaga | cccagacctt | ggcctatatg | 1800 |
| cattcactgg | ttagaatcac | tgaacttggc | caggcgcggt | gactcacgcc | tgtaatccca | 1860 |
| gcactttggg | aggccaaggt | gggtagatca | cctgaggtca | gggattccag | gccaacatgg | 1920 |
| cgaaacccca | tctctactaa | aaataccaaa | attatctggg | tgtggtggca | ggtgcctgta | 1980 |
| atcccagcta | ctcgggaggc | tgaggcagga | aaatggcttg | aacccaggag | gtgaaggctg | 2040 |
| cagtgagtcg | agatcatgcc | actgtactcc | agccaacttg | aaagttggaa | gaagtactgc | 2100 |
| gacatcgtag | aaaggagtag | ctgcccttcg | ggttgtgatt | gggcacactt | cttactcctt | 2160 |
| ctaagcttct | ctctaaagtg | ggaataacag | tacttatccc | ttagagatgt | cgtactgacc | 2220 |
| aaggataacc | atatgggcat | gccagcagag | taagtgctca | gcagtgttgc | accccagagg | 2280 |

```
cgacgtggtc atctagtgca gcattctcaa ctaggggcat ttggaaatgg gggcagggggg   2340 agttttttggt catcatggtg tctggaggct ggcagttacc tcttgggggc cacggaaagc   2400
aaatgtcctg caatgtgtgg gcagtcctgc acaatcgagt tctctcccca caaaatgtca   2460
ggagtgccag cactgagaca cacctgccca gtcccaccca ttcaggagga cacagactca   2520
gaggtgttgc cgtcttgtcc caggctctgt ggggaagctg ggatcaaacc aagtccagtg   2580
cgcttcccac tctgctctgc agcctgtttt ggttggagtt ggacctggag aaaagtcaag   2640
tcataagtca agaaagattg ggccctacta ctggaatgca ggaaaaaatg gaggagggat   2700
ggagaggttt tggaaaggca gccacagggg ttctgggaga gggaaggcat tctaagtggc   2760
agtaacagct tcagcaaagt cccaaaggtg aaaagtgcag gacacgtcc agggataagc    2820 cagtgcacta agcccacctc ttgtccccac agtccaggtg gaggccgcag agggcccagg   2880
gcaagcagag gcagcaatgg ttggtcctga cgtggctga gccccagcc cctggaatat     2940 gcagcccggg ggagccccag acagcggcaa ggacgaggtg gcggagtggg gcgggaggca   3000
tggtctccac ctaccgggtg gccgtgctgg gggcgcgagg tgtgggcaag agtgccatcg   3060
tgcgccagtt cttgtacaac gagttcagcg aggtctgcgt ccccaccacc gcccgccgcc   3120
tttacctgcc tgctgtcgtc atgaacggcc acgtgcacga cctccagatc ctcgactttc   3180
cacccatcag cgccttccct gtcaatacgc tccaggtagg aggaccctgg ggggcatggg   3240
ttagtgggga aacggatggg taggggagag gctggattcc aaactgctgt agcttgggcc   3300
ctattgccag ggccccatca ctgagtttgg gagctccaca ctgcaccttg gccactctg    3360 cttagagccg ttccaggaat ccattcattg gtgtgctagt ttattcaaca aatatttggt   3420
gaccgttcaa tgtgtgccag gccctgcagt gggcactggt gcagaatggt gagcaaaaaa   3480
tatatggaat ttgcttttcaa gaaactcata gtctggtgag aaaaggcaaa tatggtgtga   3540
taagttctat gattggagga gcagggagct ggggcagccc ttaagggggc atctaggcca   3600
tccagatgtg ttggggtgga gttggggggt cacagagggt gatgtctcaa ctaaataggt   3660
tttaggcagg taagagtcag tagagaaaag gacagggaac actaggctac tgtgagtatt   3720
cggagctgtg cctaccgtaa cctcactcca catcctctgg agaagggaca gcagcagaac   3780
agacggggcc ctgggaaagg tgtgttcttg gagactctgg agaccccagt caggtctctt   3840
gcccaaggcc ctcttctctt aagtgatgct ctgcccctga cctcaggacc tgcctgctgg   3900
gcaccctccc tgccaggttt ggatttaaat gcctgagggt cctcacttat tgtgttcctt   3960
ccccactgcc tgctggaacc aggtcctctt gccctctctc aacctctgac ttgagaggga   4020
gtggagagaa aaaggaagct gagctctagg acatgtttgc tcactgaagg aagcctctga   4080
ccagagtgta cagagctttt ccaggaagga caggcacagt ggtggaggcc cagaagacag   4140
gggacaaggc tcgtccaggt gtaactgagc aaatcaagca gtctctcagg ctgagaccct   4200
gggctgggag atggcgggca gctcagcact cagcactctc ggcaacacca ggcaggaggg   4260
ccctggccta atctgccgga gacacctgtt cacccatccc aggcacctgg ggtcaggagg   4320
aaagatggaa gcctgatccc gcatctgccc tggaagcagt gaggctgagc ctgtcagggc   4380
agacagtctg gatgcaggc cttctagttc tcttctaaag gagactttaa caatcacctg     4440
attggacatt caaatcttgc tccaagccta cacactgagc tttgttgatt tcatcttgcc   4500
ccctttacct tgattcctgc cccactctct ataaccactc ttatcgaatt tttctttctt   4560
ttttaaaatt tatttattttt ttatttttag atggagtctc cctctgtcgc ccaggctgga   4620
```

-continued

```
gtgcagtggc acgatctcgg ctcactgcaa tcttcgcctc ccgggttcaa gcgattctcc    4680
tgcctcagcc tcctgagtag ctggattaca ggcacctgcg accacaccca gctaatttt    4740 gtattttag tagagatggg gtttcaccat gttggccagg ctggtctcaa actcctgacc    4800
tcaagtgatc cgcctgccta ggcctcccaa agtactggga ttataggcat gagccaccac    4860
gcctggtctc ttatccatac tttcagtgtt tctttaccca agtaagaaaa tgcattcttc    4920
cctgcttctt acgtaaagaa caaaacaaaa acaagaacca tactgttctg taccttgatt    4980
ttattttatt tttaaaattt tttgtataga tgggtcttgc tgtgttacct aagctgatct    5040
cgaactactg gcctcaagcg atcctcctgc tttggcctct caaagtgctg ggattacaag    5100
tgtgagccac tgtgcttggc gctgtacctc aatttttta acttgctatt ataacctgaa    5160
gatttttcca ggccattatc tagaggacgt cctcattctt ttttcatggc cacgccctac    5220
tccattgaag agctatacca tggagtcctt tcttgttgga taagtgggtg gtatccagtc    5280
ttgtgctgtt tcaaacagtg ccacaatgag tggccttgta gataggtcat tttgaacata    5340
agtaggtata tctgtgggat caattaccgg aaagggcatt gctggaaatg gcactgctgg    5400
atcacaatgc ctggaaatgg cattgtgaat acagagccag gtgaggtggc tcatgcctat    5460
aatcccaaca ctttgagagg ctgaggcagg cggatcactt gagctcagga gttcgagacc    5520
agcctgggca acatgacaaa actccgtctc taccaaaaat acaaaaaatt agccaggcat    5580
ggtgctccat gcctgtggtc ccagctgctt gggaggctga ggtgggagaa tcgcctgagg    5640
ccgggaggtt gaggctgcag tgagctgaga gtgccactgc actccaactt gggtgacaga    5700
gtgaggccct gtctcaaaaa aaaaaaaaaa aagtgtgac tgtaactgga gtttggaggg    5760
gaggttattt ccagattgcc ctccatagca gtggcgtatg ctgtgctcct gtgagcaatg    5820
tatatgagag cccgttttcc tacagtcttg ccatcagagt atattgtcaa acttttgaca    5880
atatatttga caatctgaga gatgagatat gatattctcc ttgtagtctc catttgcatc    5940
tctgatcgtg ggtgaaattg agcatctttc ataggtttaa gggcctttgt gtttctcttt    6000
tcaagaacta ttgatgtcct ttgcccattt ttctattggg ttgttggctt ttttcttctt    6060
gactgaccct gagttttgga ctctaagata tccaagattt cactcctgga gcccagtaag    6120
ggacttttgg cagagaaata ctgtgaaaaa ggtatcctca aggcaccaaa gattaagtat    6180
aaaacctaag aatcctgatg gccaccatct ggaaacaaaa taatacattc ttctccaatg    6240
ccagatgaga tagagcccag gagagtagtg tttcctgggt gtgagcctca gtgtcttctg    6300
cagccccttc tatcagagaa ggaagctgag attatcaggt gcttgcaact caccaaagga    6360
attatcagca aatgcatggt tgagatgcag gtggctgagc cttgtccctg aaactggact    6420 cccttttctat tgctccttct ctgtcttgac agagccccaa gatggccttt tacagtttgg    6480
aaccctgctt cctcccttca atcaaggggg aagggataag ctagccaatc aggggccttc    6540
ctcctctctc ttttaggaac ccccagagag gagtgggtgg gaggaagcca ggagttcccc    6600
tcaaggaggc aacatgttgg gggagaggtg gggctgtcac cctcaaaagc tggcagctgc    6660
tccctctccc cagcagacag cttgaagaga ctgggagctt ctcatccctc ccacttctca    6720
ctgatctcca ttggtcttgg gggatcgtgg gagcatccgt atacacaggt tccaggctcc    6780
tggagatcac tgtgtccagc agaatgcagt cttccctggc ctaagaaacc agtttcctat    6840
ggttttaggt ttgtcctcgg catcctcccg ccgcaccaaa aatttaaacc tcagcacaaa    6900
gaaaagatgc cacacatcatct ccctagggaa atccactgca gcatcttcta agcctttgag    6960
ttgggaagtg ctgttctgaa gttggactta actctgcact actgccacca aagtcgtttc    7020
```

-continued

```
cttttgatcc ttcttggaag tggagaactg tagtcctcct ttgtgcctgg cccctgcccc    7080
actcaattca gatgctggga caggagacat acctccacct tcttctagtc ttttgcctgg    7140
gctttggtgg gagaagactc tggtttcctt tgtccttgga ggcctctgtc cccccacctt    7200
tagggacccc cttctttcca cacactggct gcctgaaacc gctcttgcag ctggcacgtt    7260
gactaatgaa tctgttaagg aaacttctct ttagtgtact tggcctttct aggagtctct    7320
tcaccttgag ctgtaccccc aatcccttga agaagttgcc acaaacattc aggaagttca    7380
tctccctgga gctgcccagg ggccctactc tacatcagcc cattatgcat ccagtctgaa    7440
tcttttctg tttctcaacc ctgagggcag agagaagcat acagaagggg cacatcaggt     7500
agcagtctaa gggcagtggc agaggcagga gttgcattga tcccagcttg gccatggag     7560
agctcaccag cccaggtagt gctattaagg agcacctgct ttgagccaac agtgctagac    7620
actcagggag gaagagggag tatatacaaa tgaggatggc ctggctgtgg ccttctcagg    7680
agctcacagc agaagtgggg aactggagat ggaacagctc taatgaaagt gtaatagaag    7740
gattgttaga acacaggaga tgaagggagt agtcccctgc ttgcaggaag gatgggaaat    7800
caggaagctt cttggaggtg gtggcacttt agctgaacct tggaagatag aattttaaca    7860
ggtccaacac ccagctcaga gctggactct tagaggtact taataaatgt acttgttgaa    7920
caaaggcctc gatggatgga tgagggcacg acatggagca aggcagagct aaactccaga    7980
tgtgcacaag acagtgcagt ggccctgtag atcaaacaat gtgacctgct ccatcctggc    8040
ttgggaatgg ggaggctaca gctcctccat tctccctggg cctggtctcc tggggatggt    8100
cgggtatgga aggcttcagg tgcagtggca ggtgagagca ctgcccctct gatgggaggt    8160
gtttggggc tagggagcc ctcatggctg ctctgaccct ggtactggct ggggatattg      8220
caggagtggg cagacacctg ctgcagggga ctccggagtg tccacgccta catcctggtc    8280
tacgacatct gctgctttga cagctttgag tacgtcaaga ccatccgcca gcagatcctg    8340
gagacgaggt gagaggctgg aacacagtcc attgccacct ctgtggatgc cccagtgcta    8400
gccagtccct gtgaaaaggg cacagtatag ggacacagat agaggtatat gtgttctaag    8460
atttccacac atacactcaa acatgcatac attgtgctgt tcccatttct gtcaactcat    8520
gttgggaccg tggctgtggg ggtggctaga gtagtgcagt agttaagaac tgggacttct    8580
ggaacaagac ttccagggcc actcagctgc atgacttgaa gccagtaaac atttaagcct    8640
atgtcctcat ctgtaaaatg gggataacag tagaacccat cttttagatc agttgtgctg    8700
atcagagaat ataacacctc cagggcttag ggctgcgcct ggagcagaac ctacggtggt    8760
ggtagtattg gccaggcaca gcctgccctg ctgggagtac agcggttgtg gggctgacag    8820
agttctgagc tgcctgcctc gccccacagg gtgatcggaa cctcagagac gcccatcatc    8880
atcgtgggca acaagcggga cctgcagcgc ggacgcgtga tcccgcgctg gaacgtgtcg    8940
cacctggtac gcaagacctg gaagtgcggc tacgtggaat gctcggccaa gtacaactgg    9000
cacatcctgc tgctcttcag cgagctgctc aagagcgtcg gctgcgcccg ttgcaagcac    9060
gtgcacgctg ccctgcgctt ccagggcgcg ctgccgcca accgctgcgc catcatgtga    9120
cgcctgcgcg ccctcgggc tgcaccggca ctggccgagc ggagggcggg gccgtactgc    9180
ggggctgggg cggggagcgg gcgggaaatg gaactgtgac ggtcccggcc tgaggcccct    9240
gcagccacgc acctcccggt gagaagcaga gcgcgagagg gagccctccg taactgccca    9300
gccctgcccc ttgcccccgt ggcttcctgg gacagccgcc ttcagtgctg tatttagtgc    9360
```

```
agtgcccggc cgacccgcg ggggtgccac agccttttgg gatggggtg agcgtgcaat     9420
ggaggctggg ggtggcgagg tgccgccttg ccgggcccc cacgtgtctt ctccagaatg    9480
tgtctgtctt tgcctggtgt cttcctttcc cgtgtccgcc caccccagcg tctgttggta   9540
cttacctgtc tcacctaccc tccagtcccc tcccagctcc gctcacaggg ctctcatttc   9600
gtccatcccc ttgtcgcaga tcctggcagc ttctttgtga ggccaggcct tctgactgtc   9660
agcaccaccg gcacagggca gagatgcggg tggcccaagg accacgatca aggggtccgg   9720
gggaccgagg tcccagatca gtgagggag aaggttgagc tctccggctt ccagggagac   9780
ctccccgccc agcagccccc agagacacaa caacctacct tccagcctta actcgatggt   9840
ccgtccctgc caggtgcccc tcactcttcc tgacccaaa gccagatcac ccctggtt     9900
aaaacttttt ttcttttttt tttttggaca gagtgtggaa agggagcccc caaaggata   9960
gcttctttt catgatgcca ggctccagtc ctttattccc ttctgcatac tgcaatctga   10020
tctgtcagac tggggaatgt tgggttctgg ggtctggtcg tgggcaggat ggtgcccaga   10080
agggggttag gttgtcccag tgaaaattct gttgccccgt ctcaacccca tctgactacc   10140
ccagactctg cctgcctcag atctcagact atcctgatta atctggggaa gaacagagcc   10200
agggaaagaa tggtgtgggac ccctgtactt gggggagaca cacctgcatc ttcctcctgc   10260
cacagatgga ggccctcagg atctgacacc ctcttgtccc aacaccagtc agccctatac  10320
cctaactcac tccaccccat tttctccggc tgcctggccg ggtttctacc tctcgtcacc   10380
ggagctgatc actgtcagtt tgtaccgat ttagaaataa caataataat gaagattcta   10440
ggaatggcat gagggattga tgggggactt ggagggaggg acaagtggtg ccctgtcccc   10500
tgctcccctg gccaaagaaa gctgtccttg aggctgagcc ctcagccctg gctggtggg   10560
gggacagcaa ggtcccttgt tataagaggg gcagagagga caactccgct ttggccaacc   10620
tagccaaggc tgcagcatat agaccaggaa atcaggtagc ccagactggt gatggagcag   10680
agtctggggg aagggtcgtg ggtgggggaat ttatcaccaa catccattgt agggggaatc   10740
tatgattctg cttccccagc ggattccac tctgtccacc aagtgggggg tagcacagcc   10800
tcacagcaac cgccctgacc ttgggcagtc tagtgttcct gcattctagt ccctgctgtg   10860
ctgcaggact ttgggcaagt gacctgccct ctgtgagcct ccctctgaca cagaggaggt   10920
ggctcccctt ccccacacct tagagtggct gggagggtaa caaagagggc ctgcccctttt  10980
agtcctcctgc acccctgccc cctggttcac cagagggagc ggatgaagga tggcagcatc   11040
tcacatgccc catcaccaac tctgaggcac ctggggtggg ggcgggagc ccaggcctct    11100
ggctgctccc ctgtgggagc cattggaatg tatcccctga caggccccct tccgcctcca   11160
cctcaaccca ggtcttggat ttcaggtccc tccaccccca ttctgagtct ctgtccttct   11220
ccttccaccc gctcccaggg tttcccacca cagggtctgg aagtgtgtgt gacgcccatt   11280
gagctgttac ccgaagtcag attaaaaatc agggagtgtt ttccctcgtt tctgtaccaa   11340
ggtgttggct ccattcctca tggtaggagg ggagggggtcc ccacagggct tgcctgctga   11400
gctccgtgtg gaaggagggt gaaggtggtg aggtggcccc cagtcccaaa gcccaggtca   11460
acagggagac caccggtgaa gagtttggga tttatcacct ttccacctaa ccccaaaccc   11520
tccagctaat tccaaccatt cagaagggaa gcagaacttc tcccctgcca ctgtctggaa   11580
aatttccata atgggactca atcccagctt ctccgtctgc gtctcgtcct tcccactcaa   11640
ggctgagact ttacagcctc tcagtcataa cttcttggat gtagatgtgt taggaacact   11700
ttcagccacc cgtcttgtcc ctgagtgatc tcaggtccca aactccagag caaagctttg   11760
```

```
aaatcttggg caagggtgcc ttgtgggagc ctgtgtgttg agggcaggac tggtctctgt   11820
ccgtggtgct gacccaccag ccacttccag gaaagatggg gctgcctggc aaggttggct   11880
gagcctcaaa agaggaagcc tctctcacca ccaactcctt ccttctagtc cccatctcct   11940
ccagtgggat aacatctgaa gctatacctc cccgcaccac cacagtcctg gagtgaggga   12000
ctcaagaagc tgggggcag ggggaggcag gttcagtggt tcacatcttt aatcccactg   12060
ctttgggagg ccaaggcagg aggatcgctt gaggccagcc tggacaacat agtaagac    12118
```

```
<210> SEQ ID NO 4
<211> LENGTH: 203
<212> TYPE: PRT
<213> ORGANISM: Human

<400> SEQUENCE: 4
```

Met Gly Gly Ser Leu Arg Val Ala Val Leu Gly Ala Pro Gly Val Gly
 1               5                  10                  15

Lys Thr Ala Ile Ile Arg Gln Phe Leu Phe Gly Asp Tyr Pro Glu Arg
             20                  25                  30

His Arg Pro Thr Asp Gly Pro Arg Leu Tyr Arg Pro Ala Val Leu Leu
         35                  40                  45

Asp Gly Ala Val Tyr Asp Leu Ser Ile Arg Asp Gly Asp Val Ala Gly
     50                  55                  60

Pro Gly Ser Ser Pro Gly Gly Pro Glu Glu Trp Pro Asp Ala Lys Asp
 65                  70                  75                  80

Trp Ser Leu Gln Asp Thr Asp Ala Phe Val Leu Val Tyr Asp Ile Cys
                 85                  90                  95

Ser Pro Asp Ser Phe Asp Tyr Val Lys Ala Leu Arg Gln Arg Ile Ala
            100                 105                 110

Glu Thr Arg Pro Ala Gly Ala Pro Glu Ala Pro Ile Leu Val Val Gly
        115                 120                 125

Asn Lys Arg Asp Arg Gln Arg Leu Arg Phe Gly Pro Arg Arg Ala Leu
    130                 135                 140

Ala Ala Leu Val Arg Arg Gly Trp Arg Cys Gly Tyr Leu Glu Cys Ser
145                 150                 155                 160

Ala Lys Tyr Asn Trp His Val Leu Arg Leu Phe Arg Glu Leu Leu Arg
                165                 170                 175

Cys Ala Leu Val Arg Ala Arg Pro Ala His Pro Ala Leu Arg Leu Gln
            180                 185                 190

Gly Ala Leu His Pro Ala Arg Cys Ser Leu Met
        195                 200

```
<210> SEQ ID NO 5
<211> LENGTH: 4
<212> TYPE: PRT
<213> ORGANISM: Homo sapien

<400> SEQUENCE: 5
```

Asn Val Ser His
 1

```
<210> SEQ ID NO 6
<211> LENGTH: 4
<212> TYPE: PRT
<213> ORGANISM: Homo sapien

<400> SEQUENCE: 6
```

Thr Leu Gln Glu
1

<210> SEQ ID NO 7
<211> LENGTH: 6
<212> TYPE: PRT
<213> ORGANISM: Homo sapien

<400> SEQUENCE: 7

Gly Val Gly Lys Ser Ala
1               5

<210> SEQ ID NO 8
<211> LENGTH: 6
<212> TYPE: PRT
<213> ORGANISM: Homo sapien

<400> SEQUENCE: 8

Gly Cys Ala Arg Cys Lys
1               5

<210> SEQ ID NO 9
<211> LENGTH: 4
<212> TYPE: PRT
<213> ORGANISM: Homo sapien

<400> SEQUENCE: 9

Cys Ala Ile Met
1

<210> SEQ ID NO 10
<211> LENGTH: 8
<212> TYPE: PRT
<213> ORGANISM: Homo sapien

<400> SEQUENCE: 10

Gly Ala Arg Gly Val Gly Lys Ser
1               5

<210> SEQ ID NO 11
<211> LENGTH: 601
<212> TYPE: DNA
<213> ORGANISM: Homo sapien

<400> SEQUENCE: 11

```
ctccttctaa gcttctctct aaagtgggaa taacagtact tatcccttag agatgtcgta      60
ctgaccaagg ataaccatat gggcatgcca gcagagtaag tgctcagcag tgttgcaccc     120
cagaggcgac gtggtcatct agtgcagcat tctcaactag gggcatttgg aaatgggggc     180
agggggagtt tttggtcatc atggtgtctg gaggctggca gttacctctt gggggccacg     240
gaaagcaaat gtcctgcaat gtgtgggcag tcctgcacaa tcgagttctc tccccacaaa     300
mtgtcaggag tgccagcact gagacacacc tgcccagtcc cacccattca ggaggacaca     360
gactcagagg tgttgccgtc ttgtcccagg ctctgtgggg aagctgggat caaaccaagt     420
ccagtgcgct tcccactctg ctctgcagcc tgttttggtt ggagttggac ctggagaaaa     480
gtcaagtcat aagtcaagaa agattgggcc tactactgg aatgcaggaa aaatggagg      540
agggatggag aggttttgga aagcagcca cagggttct gggagaggga aggcattcta      600
a                                                                    601
```

<210> SEQ ID NO 12

<211> LENGTH: 601
<212> TYPE: DNA
<213> ORGANISM: Homo sapien

<400> SEQUENCE: 12

| | | | | | | |
|---|---|---|---|---|---|---|
| tgcccagtcc | cacccattca | ggaggacaca | gactcagagg | tgttgccgtc | ttgtcccagg | 60 |
| ctctgtgggg | aagctgggat | caaaccaagt | ccagtgcgct | tcccactctg | ctctgcagcc | 120 |
| tgttttggtt | ggagttggac | ctggagaaaa | gtcaagtcat | aagtcaagaa | agattgggcc | 180 |
| ctactactgg | aatgcaggaa | aaatggagg | agggatggag | aggttttgga | aaggcagcca | 240 |
| caggggttct | gggagaggga | aggcattcta | agtggcagta | acagcttcag | caaagtccca | 300 |
| raggtggaaa | agtgcaggac | acgtccaggg | ataagccagt | gcactaagcc | cacctcttgt | 360 |
| ccccacagtc | caggtggagg | ccgcagaggg | cccagggcaa | gcagaggcag | caatggttgg | 420 |
| tcctgacggt | ggctgagccc | ccagcccctg | aatatgcag | cccggggag | ccccagacag | 480 |
| cggcaaggac | gaggtggcgg | agtggggcgg | gaggcatggt | ctccacctac | cgggtggccg | 540 |
| tgctggggc | gcgaggtgtg | ggcaagagtg | ccatcgtgcg | ccagttcttg | tacaacgagt | 600 |
| t | | | | | | 601 |

<210> SEQ ID NO 13
<211> LENGTH: 601
<212> TYPE: DNA
<213> ORGANISM: Homo sapien

<400> SEQUENCE: 13

| | | | | | | |
|---|---|---|---|---|---|---|
| acccatcagc | gccttccctg | tcaatacgct | ccaggtagga | ggaccctggg | gggcatgggt | 60 |
| tagtggggaa | acgatgggt | aggggagagg | ctggattcca | aactgctgta | gcttgggccc | 120 |
| tattgccagg | gccccatcac | tgagtttggg | agctccacac | tgcaccttgg | gccactctgc | 180 |
| ttagagccgt | tccaggaatc | cattcattgg | tgtgctagtt | tattcaacaa | atatttggtg | 240 |
| accgttcaat | gtgtgccagg | ccctgcagtg | ggcactggtg | cagaatggtg | agcaaaaaat | 300 |
| wtatggaatt | tgcttcaag | aaactcatag | tctggtgaga | aaaggcaaat | atggtgtgat | 360 |
| aagttctatg | attggaggag | cagggagctg | gggcagccct | taaggggca | tctaggccat | 420 |
| ccagatgtgt | tggggtggag | ttgggggtc | acagagggtg | atgtctcaac | taaataggtt | 480 |
| ttaggcaggt | aagagtcagt | agagaaaagg | acagggaaca | ctaggctact | gtgagtattc | 540 |
| ggagctgtgc | ctaccgtaac | ctcactccac | atcctctgga | gaagggacag | cagcagaaca | 600 |
| g | | | | | | 601 |

<210> SEQ ID NO 14
<211> LENGTH: 601
<212> TYPE: DNA
<213> ORGANISM: Homo sapien

<400> SEQUENCE: 14

| | | | | | | |
|---|---|---|---|---|---|---|
| gacaatctga | gagatgagat | atgatatcct | ccttgtagtc | tccatttgca | tctctgatcg | 60 |
| tgggtgaaat | tgagcatctt | tcataggttt | aagggccttt | gtgtttctct | tttcaagaac | 120 |
| tattgatgtc | ctttgcccat | ttttctattg | ggttgttggc | tttttttcttc | ttgactgacc | 180 |
| ctgagttttg | gactctaaga | tatccaagat | ttcactcctg | gagcccagta | agggactttt | 240 |
| ggcagagaaa | tactgtgaaa | aaggtatcct | caaggcacca | aagattaagt | ataaaaccta | 300 |
| rgaatcctga | tggccaccat | ctggaaacaa | aataatacat | tcttctccaa | tgccagatga | 360 |
| gatagagccc | aggagagtag | tgtttcctgg | gtgtgagcct | cagtgtcttc | tgcagcccct | 420 |

```
tctatcagag aaggaagctg agattatcag gtgcttgcaa ctcaccaaag gaattatcag    480
caaatgcatg gttgagatgc aggtggctga gccttgtccc tgaaactgga ctcccttcct    540
attgctcctt ctctgtcttg acagagcccc aagatggcct tttacagttt ggaaccctgc    600
t                                                                   601
```

```
<210> SEQ ID NO 15
<211> LENGTH: 601
<212> TYPE: DNA
<213> ORGANISM: Homo sapien

<400> SEQUENCE: 15
aatcctgatg gccaccatct ggaaacaaaa taatacattc ttctccaatg ccagatgaga     60
tagagcccag gagagtagtg tttcctgggt gtgagcctca gtgtcttctg cagccccttc    120
tatcagagaa ggaagctgag attatcaggt gcttgcaact caccaaagga attatcagca    180
aatgcatggt tgagatgcag gtggctgagc cttgtccctg aaactggact cccttctat    240 tgctccttct ctgtcttgac agagcccaa gatggccttt tacagtttgg aaccctgctt    300
yctcccttca atcaagggg aagggataag ctagccaatc aggggccttc ctcctctctc    360
ttttaggaac ccccagagag gagtgggtgg gaggaagcca ggagttcccc tcaaggaggc    420
aacatgttgg gggagaggtg gggctgtcac cctcaaaagc tggcagctgc tccctctccc    480
cagcagacag cttgaagaga ctgggagctt ctcatccctc ccacttctca ctgatctcca    540
ttggtcttgg gggatcgtgg gagcatccgt atacacaggt tccaggctcc tggagatcac    600
t                                                                   601
```

```
<210> SEQ ID NO 16
<211> LENGTH: 601
<212> TYPE: DNA
<213> ORGANISM: Homo sapien

<400> SEQUENCE: 16
gtcctccttt gtgcctggcc cctgccccac tcaattcaga tgctgggaca ggagacatac     60
ctccaccttc ttctagtctt ttgcctgggc tttggtggga gaagactctg gtttcctttg    120
tccttggagg cctctgtccc cccacccttta gggaccccct tctttccaca cactggctgc    180
ctgaaaccgc tcttgcagct ggcacgttga ctaatgaatc tgttaaggaa acttctctt    240 agtgtacttg gcctttctag gagtctcttc accttgagct gtaccccca atcccttgag    300 wagttgccac aaacattcag gaagttcatc tccctggagc tgcccagggg ccctactcta    360
catcagccca ttatgcatcc agtctgaatc tttttctgtt tctcaaccct gagggcagag    420
agaagcatac agaagggca catcaggtag cagtctaagg gcagtggcag aggcaggagt    480
tgcattgatc ccagcttggg ccatggagag ctcaccagcc caggtagtgc tattaaggag    540
cacctgcttt gagccaacag tgctagacac tcagggagga gagggagta tatacaaatg    600 a                                                                   601
```

```
<210> SEQ ID NO 17
<211> LENGTH: 601
<212> TYPE: DNA
<213> ORGANISM: Homo sapien

<400> SEQUENCE: 17
tgccccagtg ctagccagtc cctgtgaaaa gggcacagta tagggacaca gatagaggta     60
```

-continued

| | |
|---|---|
| tatgtgttct aagatttcca cacatacact caaacatgca tacattgtgc tgttcccatt | 120 |
| tctgtcaact catgttggga ccgtggctgt gggggtggct agagtagtgc agtagttaag | 180 |
| aactgggact tctggaacaa gacttccagg gccactcagc tgcatgactt gaagccagta | 240 |
| aacatttaag cctatgtcct catctgtaaa atggggataa cagtagaacc catcttttag | 300 |
| rtcagttgtg ctgatcagag aatataacac ctccagggct tagggctgcg cctggagcag | 360 |
| aacctacggt ggtggtagta ttggccaggc acagcctgcc ctgctgggag tacagcggtt | 420 |
| gtggggctga cagagttctg agctgcctgc ctcgccccac agggtgatcg aacctcaga | 480 |
| gacgcccatc atcatcgtgg gcaacaagcg ggacctgcag cgcggacgcg tgatcccgcg | 540 |
| ctggaacgtg tcgcacctgg tacgcaagac ctggaagtgc ggctacgtgg aatgctcggc | 600 |
| c | 601 |

<210> SEQ ID NO 18
<211> LENGTH: 601
<212> TYPE: DNA
<213> ORGANISM: Homo sapien

<400> SEQUENCE: 18

| | |
|---|---|
| tgccctgtcc cctgctcccc tggccaaaga aagctgtcct tgaggctgag ccctcagccc | 60 |
| tggcctggtg gggggacagc aagtcccctt gttataagag gggcagagag gacaactccg | 120 |
| ctttggccaa cctagccaag gctgcagcat atagaccagg aaatcaggta gcccagactg | 180 |
| gtgatggagc agagtctggg ggaagggtcg tgggtgggga atttatcacc aacatccatt | 240 |
| gtaggggaa tctatgattc tgcttcccca gcggattccc actctgtcca ccaagtgggg | 300 |
| sgtagcacag cctcacagca accgccctga ccttgggcag tctagtgttc ctgcattcta | 360 |
| gtccctgctg tgctgcagga ctttgggcaa gtgacctgcc ctctgtgagc ctccctctga | 420 |
| cacagaggag gtggctcccc ttccccacac cttagagtgg ctgggagggt aacaaagagg | 480 |
| gcctgcccct ttagtctcct gcacccctgc ccctggttc accagaggga gcggatgaag | 540 |
| gatggcagca tctcacatgc cccatcacca actctgaggc acctggggtg gggggcgga | 600 |
| g | 601 |

<210> SEQ ID NO 19
<211> LENGTH: 601
<212> TYPE: DNA
<213> ORGANISM: Homo sapien

<400> SEQUENCE: 19

| | |
|---|---|
| ccaagtgggg ggtagcacag cctcacagca accgccctga ccttgggcag tctagtgttc | 60 |
| ctgcattcta gtccctgctg tgctgcagga ctttgggcaa gtgacctgcc ctctgtgagc | 120 |
| ctccctctga cacagaggag gtggctcccc ttccccacac cttagagtgg ctgggagggt | 180 |
| aacaaagagg gcctgcccct ttagtctcct gcacccctgc ccctggttc accagaggga | 240 |
| gcggatgaag gatggcagca tctcacatgc cccatcacca actctgaggc acctggggtg | 300 |
| rgggggcgga gcccaggcct ctggctgctc cctgtggga gccattggaa tgtatcccct | 360 |
| gacaggcccc cttccgcctc cacctcaacc caggtcttgg atttcaggtc cctccacccc | 420 |
| cattctgagt ctctgtcctt ctccttccac ccgctcccag ggtttccac cacagggtct | 480 |
| ggaagtgtgt gtgacgccca ttgagctgtt acccgaagtc agattaaaaa tcagggagtg | 540 |
| ttttcccctcg tttctgtacc aaggtgttgg ctccattcct catggtagga ggggagggt | 600 |
| c | 601 |

```
<210> SEQ ID NO 20
<211> LENGTH: 332
<212> TYPE: DNA
<213> ORGANISM: Homo sapien

<400> SEQUENCE: 20
gagcctgtgt gttgagggca ggactggtct ctgtccgtgg tgctgaccca ccagccactt      60
ccaggaaaga tggggctgcc tggcaaggtt ggctgagcct caaaagagga agcctctctc     120
accaccaact ccttccttct agtccccatc tcctccagtg ggataacatc tgaagctata     180
cctccccgca ccaccacagt cctggagtga gggactcaag aagctggggg gcaggggag     240 gcaggttcag tggttcacat ctttaatccc actgctttgg gaggccaagg caggaggatc     300
rcttgaggcc agcctggaca acatagtaag ac                                   332
```